US006964779B1

(12) United States Patent
Hayakawa et al.

(10) Patent No.: US 6,964,779 B1
(45) **Date of Patent: *Nov. 15, 2005**

(54) TABLET MANUFACTURING METHOD AND TABLET

(75) Inventors: Eiji Hayakawa, Susono (JP); Yasuhiro Ishikawa, Shizuoka (JP); Tomohiko Goto, Shizuoka (JP); Kiyoshi Morimoto, Mishima (JP); Kunio Ito, Shizuoka (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/647,786

(22) PCT Filed: Apr. 7, 1999

(86) PCT No.: PCT/JP99/01861

§ 371 (c)(1),
(2), (4) Date: Dec. 18, 2000

(87) PCT Pub. No.: WO99/52491

PCT Pub. Date: Oct. 21, 1999

(30) Foreign Application Priority Data

Apr. 8, 1998 (JP) ................................ 10-096441

(51) Int. Cl.[7] ................................................ A61K 9/20

(52) U.S. Cl. ....................... 424/465; 424/464; 424/474

(58) Field of Search ................................ 424/465, 464, 424/474; 428/403; 264/109, 299, 309, 319

(56) References Cited

U.S. PATENT DOCUMENTS

| | | | | |
|---|---|---|---|---|
| 3,461,195 | A * | 8/1969 | Sebastiani | 264/109 |
| 4,047,866 | A * | 9/1977 | Shah | 425/107 |
| 4,323,530 | A | 4/1982 | Voss et al. | |
| 4,373,888 | A | 2/1983 | Yamamoto | |
| 4,832,880 | A | 5/1989 | Staniforth | 264/22 |
| 5,093,372 | A | 3/1992 | Uedo et al. | 514/687 |
| 5,126,145 | A * | 6/1992 | Evenstad et al. | 424/465 |
| 5,356,577 | A | 10/1994 | Boldis et al. | |
| 6,432,534 | B1 * | 8/2002 | Hayakawa et al. | 428/403 |
| 6,765,695 | B2 * | 7/2004 | Chen et al. | 358/1.9 |

FOREIGN PATENT DOCUMENTS

EP 0 650 826 A1 5/1995

OTHER PUBLICATIONS

JP 45-22959 (8/70) Abstract.

* cited by examiner

*Primary Examiner*—Jyothsna Venkat
(74) *Attorney, Agent, or Firm*—Fitzpatrick, Cella, Harper & Scinto

(57) ABSTRACT

According to the tablet production method of the present invention, tablet is produced by compressing molding material by means of punches and dies comprising the steps of using powdered or granular material including compound which is denaturalized or inactivated when tabletted at high pressure is used as the molding material, housing the punches and the dies in a spraying chamber, generating pulsating vibration air and spraying lubricant mixed in air in the spraying chamber, applying the lubricant on the surfaces of the punches and the dies while the lubricant sprayed in the spraying chamber is mixed with the pulsating vibration air, and tabletting the molding material by means of the punches applied with the lubricant on the surface thereof and the dies applied with the lubricant on the surface thereof.

14 Claims, 18 Drawing Sheets

(a)

(b)

(a)

(b)

(a)

(b)

(c)

TABLET MANUFACTURING METHOD AND TABLET

TECHNICAL FIELD

The present invention relates to a tablet production method, particularly to a tablet production method wherein a tablet including compound powdered or granulated which is apt to be denaturalized or inactivated when tabletted at high pressure can be manufactured without denaturalizing or deactivating drugs and also to a tablet production method wherein a tablet including solid dispersion powdered or granulated can be manufactured while keeping the function of the solid dispersion powdered or granulated.

The present invention also relates to a tablet including compound powdered or granulated which is denaturalized or inactivated when tabletted at high pressure without denaturalized or inactivated and also to a tablet including solid dispersion powdered or granulated keeping the function thereof.

BACKGROUND ART

A tablet has an advantage of easy dosing and is the most preferable type for patient as oral administration and intrabuccal administration.

Such a tablet is generally produced by an internal lubricant method and an external lubricant spraying method.

According to the internal lubricant method, in order to prevent that molding material to be tabletted is apt to attach on punches and dies and gride between the punches and dies is apt to be caused so as to execute smooth tabletting and also prevent defective goods with sticking, capping or laminating, magnesium stearate, lauryl sodium sulphate, talc and so on are mixed in the molding material to be tabletted other than active compound and diluting agent and the mixture is compressed to obtain a tablet.

As an external lubricant spraying method, a tablet production method has been disclosed in, for example, JP-B-41-11273 and JP-A-56-14098.

FIG. 17 schematically shows procedures of the tablet production method disclosed in JP-B-41-11273.

According to the method comprised of charging a fixed amount of material to be tabletted in a die, tabletting the charged material in the die by means of a pair of an upper and a lower punches, and discharging the tablet, as a procedure before molding material is charged in the die 151 as shown in FIG. 17(*a*), a spray nozzle 159 for spraying lubricant L is provided above the die 151 and lubricant L is applied on a lower surface 153*s* of the upper punch 153 and an upper surface 154*s* of the lower punch 154, both of which are provided for the die 151 which comes to a place where the spray nozzle 159 is placed. Then molding material is charged in the die 151 as shown in FIG. 17(*b*), and the charged material m is compressed by means of the upper punch 153 on which lower surface 153*s* is applied with lubricant L and the lower punch 154 of which upper surface 154*s* is applied with lubricant as shown in FIG. 17(*c*).

The member indicated by the numeral 152 in FIG. 17 shows a rotary table provided with the die 151 (The same numeral is used in FIG. 18).

FIG. 18 shows a tablet production method described in JP-A-56-14098.

According to this method, before molding material is charged in a die 151, a spray 156 for spraying lubricant L and a nozzle 159 for spraying air are provided above the die 151. Lubricant L is sprayed in the spray 156 when the die 151 comes where the spray 156 is provided as shown in FIG. 18(*a*), lubricant is applied on an upper surface 154*s* of a lower punch 154 provided for the die 151 as shown in FIG. 18(*b*). As shown in FIG. 18(*c*), compressed air is sprayed on the lower punch 154 at a position where the nozzle 159 is provided, lubricant L applied on the upper surface 154*s* of the lower punch 154 is blown upwardly to be dispersed, then the dispersed lubricant L is attached on an inner wall 151*s* of the die 151 and a lower surface 153*s* of an upper punch 153. Thereafter, molding material m is compressed to produce a tablet by means of lubricated inner wall 151*s* of the die 151, lubricated lower surface 153*s* of the upper punch 153, and lubricated upper surface 154*s* of the lower punch 154.

However, some drugs are destabilized or dissolved or its elution becomes slow because its crystal is deformed by the pressure applied at the time of tabletting (usually 1 ton/c $m^2$–2 ton/c $m^2$), friction, and heating. (Hereinafter such substances are called "drugs which is denaturalized or inactivated when tabletted at high pressure" in this specification.)

As a method for tabletting such drugs, an internal lubricant method wherein lubricant such as macrogol 6000, sucrose esters of fatty acid, and so on are added to molding material has been already suggested. (Refer to the summary of $11^{th}$ pharmaceuticals and powder design symposium, 79 (1994) and JP-A-8-175996.)

Solid dispersing pharmaceuticals wherein compound is dispersed in low molecular carrier or high molecular carrier has been recently developed.

Such solid dispersing pharmaceuticals are highly effective to heighten solubility of drugs which is slight soluble and has low absorbability into the body in case of oral dosage, to control releasing speed of drugs, and to improve bioavailability of drugs.

Solid dispersion pharmaceuticals are generally produced by a fusion method wherein drugs and carrier are heated and fused and thereafter cooled down. Or they are produced by means of a solvent method wherein drugs and carrier are dissolved in an appropriate solvent and the solvent is removed. Or they are produced by a fusion-solvent method wherein a fusion method and a solvent method are combined.

However, an internal lubricant means wherein a tablet including compound which are denaturalized or inactivated when tabletted at high pressure is produced by adding lubricant such as macrogol 6000, sucrose esters of fatty acid, and so on in molding material isn't an adequate method. According to drugs, compressed tablet may be destabilized or decomposed, or elution may become slow even if lubricant such as macrogol 6000, sucrose esters of fatty acid, and so on is added to molding material.

Further, depending on drugs, they may attach on punches and dies at the time of tabletting. As the result, produced tablet may cause sticking, capping and laminating.

When solid dispersion is produced into a tablet as solid dispersing pharmaceuticals wherein solid dispersion is pulverized into a suitable particle size and the pulverized substance and lubricant are mixed according to the prior internal lubricant method, property of the solid dispersion tablet may be changed because of water repellency of lubricant included in the tablet. When lubricant is included in the tablet, high pressure is required to give practical hardness. However, the solid dispersion may be denaturalized because of high tabletting pressure and originally designed property (for example disintegrating time) isn't achieved.

Therefore, pharmaceuticals including drugs which are denaturalized or inactivated when tabletted at high pressure and solid dispersing pharmaceuticals are generally supplied as capsule in the market so far.

However, capsule is hard to be taken for elderly person and children because it floats on the water when taking with water. It has been requested by physician and so on to develop a tablet which sinks in the water and is easy to be swallowed when taking with water as pharmaceuticals including drugs which are denaturalized or inactivated when tabletted at high pressure and as solid dispersing pharmaceuticals.

Also capsule needs a body and a cap and its production takes a lot of labor as follows. Drugs which are denaturalized or in activated when tabletted a thigh-pressure and solid dispersion (powder and granule) are pulverized and charged in the body of capsule and the cap is covered thereon to be sealed.

Further, physician requests not only that pharmaceuticals conventionally supplied as capsule in the market is produced as a tablet but also that such tablet is dividable so that patient can take appropriate dosage.

The present invention has been developed in order to solve the above-mentioned problems. The object of the present invention is to provide a production method of tablet wherein a tablet including compound powdered or granulated which is denaturalized or inactivated when tabletted at high pressure can be easily produced without denaturalizing or deactivating such compound.

Another objet of the invention is to provide a tablet including solid dispersion powdered or granulated keeping function of the solid dispersing material, a tablet including compound which is denaturalized or inactivated when tabletted at high pressure without denaturalizing or deactivating such compound, and a dividable type tablet of these tablets which can keep its function when divided.

DISCLOSURE OF THE INVENTION

The tablet production method in the present invention is a tabletting method for compressing molding material by means of punches and dies. Powdered or granular material including compound which is denaturalized or inactivated when tabletted at high pressure is used as the molding material. The punches and the dies are housed in a spraying chamber. Pulsating vibration air is generated, and lubricant mixed in air is sprayed in the spraying chamber. The surfaces of punches and dies are applied with lubricant while lubricant sprayed in the spraying chamber is mixed with pulsating vibration air. Then molding material is tabletted by means of the punches and dies applied with the lubricant on the surface thereon.

Here in this specification "high pressure" means a required tabletting pressure for compressing molding material by an internal lubricant method and for producing a tablet having practical hardness. More specifically it means greater than or equal to 1 ton/cm$^2$.

"Compound powdered or granulated which is denaturalized or inactivated when tabletted at high pressure" means powdered and granule of compound which is apt to be denaturalized or inactivated when tabletted by means of an internal lubricant method. Specifically the examples of such compound are pharmaceuticals shown in the following tables 3–6, explained hereinafter.

"Powdered or granular material including compound powdered or granulated which is denaturalized or inactivated when tabletted at high pressure" may include diluting agent, binder, supplement such as solution adjuvant, solubilizer and disintegrant, corrigent, colorant, adjuvant for pharmaceuticals, antioxidant, preservative, opacifying agent, charge protector, aroma, sweetening agent, fluidizing agent, flavoring agent, and so on, if required, other than compound powdered or granulated which is denaturalized or inactivated when tabletted at high pressure. However, it doesn't include lubricant.

According to this production method, lubricant is sprayed in the spraying chamber wherein pulsating vibration air is generated and lubricant mixed with pulsating vibration air is applied on the surfaces of punches and dies. Comparing with prior external lubricant spraying method, lubricant can be uniformly applied on the surfaces of the punches and dies.

As a result, under the process wherein compound which is denaturalized or inactivated when tabletted at high pressure is tabletted, the compound is hard to be attached on the surfaces of the punches and dies so that such tablet as biochemical pharmaceuticals is produced without sticking, capping and laminating.

Moreover, lubricant is merely attached on the surface of tablet and isn't included inside of tablet. Therefore, comparing with a tablet including lubricant, produced tablet has practical hardness even if compound powdered or granulated which is denaturalized or inactivated when tabletted at high pressure is tabletted at low pressure (concretely under 1 ton/c m$^2$.

Several kinds of lubricant can be used for tablet production method of the present invention. Lubricant isn't specifically limited, for example, there are stearate acid metal salt (magnesium stearate, calcium stearate and so on), stearic acid, sodium lauryl sulfate, sodium lauryl magnesium, powdered gum arabic, carnauba wax, anhydrous silicic acid, magnesium oxide, silic acid hydrate, boric acid, fatty acid sodium salt, leucine, and so on which have been commonly used. One of them may be used solely or more than two of them may be combined.

As for diluting agent, there are several kinds, such as saccharides (lactose, sucrose, glucose, mannitol, and so on), starch (for example, potato, wheat, corn and so on), inorganic substance (calcium carbonate, calcium sulfate, sodium bicarbonate, sodium chloride, and soon), crystalline cellulose, powdered plant (powdered glycyrrhiza, powdered gentian, and so on).

Moreover, any kind of pulsating vibration air with different cycle and strength, regardless of positive pressure or negative pressure, may be used if air pressure of pulsating vibration air can achieve function of forcibly diffusing lubricant particle sprayed in the sampling chamber by generating air vibration all over the sampling chamber.

Conditions such as frequency and pressure of pulsating vibration air depend on size and shape of punches and dies of a tabletting machine, size and shape of a spraying chamber, how a lubricant spraying means is provided, and description of active compound. Therefore, conditions can't be simply defined and is defined based on experiments.

According to a preferred tablet production method, molding material is compressed by means of punches and dies. The method uses solid dispersion powdered or granulated molding material. The punches and the dies are housed in a spraying chamber, pulsating vibration air is generated therein, and lubricant mixed in air is sprayed. The lubricant is applied on the surfaces of the punches and the dies while the lubricant sprayed in the spraying chamber is mixed with the pulsating vibration air and the molding material is tabletted by the lubricated punches and the lubricated dies.

"Solid dispersion powdered or granulated" in this specification means solid dispersion (powder or granule) ground into appropriate particle size.

More concretely explained, this tablet production method is effective for tabletting solid dispersion powdered or granulated including low molecule compounds of which elution is delayed and high molecule compounds which is apt to be dissolved and denaturalized when tabletted at high pressure according to an internal lubricant method.

As a carrier of solid dispersion, so called high molecule carrier can be used.

Generally there are pH dependent high molecular carrier, pH independent high molecular carrier, water-soluble high molecular carrier, and so on. Examples are as follows:

hydroxypropylmethylcellulose phthalate 220824 (HP50), hydroxypropylmethylcellulose phthalate 220731 (HP55), hydroxypropylmethylcellulose acetate succinate (A coat), carboxymethylethylcellulose (CMBC), cellulose acetate phthalate (CAP), metaacrylic acid copolymer LD (L30D55), meta acrylic acid copolymer S(S-100), aminoalkylmetaacylate copolymer E (soluble in stomach), polyvinyl acetal diethyl amino acetate (ABA), polyvinylpyrrolidone (K-25, 30, 90; PVP), ethyl cellulose (BC), metacrylic acid copolymer RS (RS30D), polyvinyl alcohol (PVA), metylcellulose (MC), hydroxypropylcellulose (HPC), hydroxypropylmethylcellulose 2208 (METROSE 90SH), hydroxypropylmethylcellulose 2906 (METOLOSE 65SH), hydroxypropylmethylcellulose 2910 (METROLSE 60SH, TC-5R), sodium carboxymethylcellulose, dextrin, pullulane, gum arabic, tragacanth, propylene glocol alginate, agar powder, gelatin, starch, processed starch, phospholipid (lecithin), glucomannnan glucomannnan, and so on.

Such high molecular carrier may be used solely or some of them may be combined if required.

Particle size of high molecular carrier is usually less than or equal to 7000 μm, more preferably less than or equal to 2000 μm. Conditions such as pressure, temperature, supplying speed, adding amount and supplying speed of water or plasticizer, and so on, according to the present invention, differ depending on the kind of used drugs, high molecular carrier, dual-axis extruder, and so on. However, it is important to combine them so as to lower molding temperature under decomposition temperature of drugs and high molecular carrier. And it is also important to change them according to product characteristic expected to be produced.

The ratio (weight ratio) when drugs and high molecular carrier are mixed differs depending on kinds, object, membrane characteristic, and so on thereof. It is suitable at 0.1–999 of high molecular carrier for 1 drug, preferably 0.5–500, more preferably 1–50.

In a material including both compound which is unstable for heat and high molecular carrier, water solution or dispersant of plasticizer can be added to the material when or before the material is extruded with the dual-axis extruder. When this method is utilized, temperature of transition of high molecular carrier can be lowered. Therefore, molding temperature can be lower than the decomposition temperature of compound and high molecular carrier so that decomposition caused by the heat of drugs and high molecular carrier can be prevented. Of course, in a material which doesn't include both compound which is unstable for heat and high molecular carrier, water solution or dispersant of plasticizer can be added in a same manner.

As plasticizer for lowering the temperature of transition of high molecular carrier, compound which has been used as plasticizer for film coating in the field of manufacturing technique can be used. Such a compound is as follows;

cetanol, fatty acid polyoxyethylene-polyoxyp, macrogol (200, 300, 400, 600, 1000, 1500, 1540, 4000, 6000, 20000), triacetyne, triethyl citric (cytroflex), and so on.

Adding amount of plasticizer depends on used drugs and high molecular carrier, however its ratio is suitable at 1%–80% for a molecular carrier, preferably at 5%–50%.

Plasticizer may be directly added to the mixture of high molecular carrier and drugs at first or plasticizer dissolved or deipersed in the water may be added during molding. Adding method of platicizer isn't limited.

According to this tablet production method, lubricant is sprayed in the spraying chamber wherein pulsating vibration air is generated and the lubricant mixed with pulsating vibration air is applied on the surfaces of punches and dies. Therefore, lubricant can be applied uniformly on the surfaces of the punches and dies comparing with the prior external lubricant spraying means.

As the result, molding material hardly attaches on the surfaces of punches and dies in tabletting step of solid dispersion powdered or granulated so that produced tablet of solid dispersion doesn't cause sticking, capping and laminating.

Further, lubricant is attached only on the surface of produced tablet of solid dispersion and isn't included therein. Therefore, produced tablet of solid dispersion has practical hardness even if solid dispersion powdered or granulated is tabletted at low tabletting pressure comparing with a tablet of solid dispersion including lubricant therein.

According to this tablet production method, tablet of solid dispersion substance can be tabletted at low tabletting pressure so that property of solid dispersion substance isn't changed.

According to the tablet production method for compressing molding material by means of punches and dies, powdered or granular material, including compound which is denaturalized or inactivated when tabletted at high pressure, is used as molding material. The punches and the dies are housed in a spraying chamber, the lubricant is applied on the surfaces of the punches and the dies while the lubricant sprayed in the spraying chamber is mixed with positive pulsating vibration air, and the molding material is tabletted by the punches applied with the lubricant on the surface thereof, and the dies applied with the lubricant on the surface thereof.

According to this production method, lubricant mixed with positive pulsating vibration air is sprayed in the spraying chamber and is applied on the surfaces of the punches and dies. Lubricant can be uniformly applied on the surfaces of the punches and dies comparing with the prior external lubricant spraying method.

As a result, when tabletting compound powdered or granulated which is denaturalized or inactivated when tabletted at high pressure, such compound as denaturalized or inactivated when tabletted at high pressure hardly attaches on the surface of the punches and dies and produced biological pharmaceuticals doesn't cause sticking, capping, laminating, and so on.

Further, lubricant is attached only on the surfaces of tablet and isn't included therein. Produced tablet has practical hardness even if compound which is denaturalized or inactivated when tabletted at high pressure is tabletted at low tabletting pressure (concretely less than or equal to 1 ton/$cm^2$) comparing with the tablet including lubricant.

According to another tablet production method for compressing molding material by means of punches and dies, solid dispersion powdered or granulated material is used for molding. The punches and the dies are housed in a spraying chamber, lubricant is applied on the surfaces of the punches and the dies while the lubricant sprayed in the spraying chamber is mixed with positive pulsating vibration air, and the molding material is tabletted by the punches applied with the lubricant on the surface thereof, and the dies applied with the lubricant on the surface thereof.

According to this method, lubricant mixed with positive pulsating vibration air is sprayed in the spraying chamber and the mixed lubricant is applied on the surfaces of the punches and dies. Therefore, lubricant can be uniformly applied on the surfaces of the punches and dies comparing with the prior external lubricant spraying means.

As the result, molding material hardly attaches on the surfaces of the punches and dies when solid dispersion powdered or granulated is tabletted and produced tablet of solid dispersion doesn't cause sticking, capping, laminating and so on.

Further lubricant is attached only on the surface of produced tablet of solid dispersion and isn't included therein. Therefore, the produced tablet of solid dispersion has a hardness of practical level even if solid dispersion powdered or granulated is compressed at low tabletting pressure comparing with the tablet of solid dispersion including lubricant therein.

According to this tablet production method, solid dispersion can be tabletted at low tabletting pressure so that property of solid dispersion isn't changed.

According to the tablet production method, spraying amount per tablet in the sampling chamber is preferably greater than or equal to 0.0001 weight percent and less than or equal to 0.2 weight percent.

The amount of lubricant is preferably reduced as far as possible in order to prevent disintegration time of tablet from extending and to prevent hardness of tablet from lowering. The amount of lubricant per tablet is preferably greater than or equal to 0.0001 weight % and less than or equal to 0.2 weight %, more preferably greater than or equal to 0.01 weight % and less than or equal to 0.1 weight %.

According to this production method, lubricant amount per tablet is set greater than or equal to 0.0001 weight % and less than or equal to 0.2 weight %. Therefore disintegration time of tablet doesn't extend and hardness of tablet doesn't deteriorated.

According to the tablet production method, the punches may be provided with a projected line for dividing of a tablet.

In this tablet production method, the punches are provided with a projected line for forming a dividing line of a tablet so that a dividable tablet including powdered or granular compound which is denaturalized or inactivated when tabletted at high pressure and a dividable tablet including solid dispersion powdered or granulated of which function isn't damaged.

The tablet production method is desirably characterized in that the following steps are continuously executed; housing the punches and the dies in the sampling chamber; generating pulsating vibration air, spraying lubricant mixed in air in the spraying chamber, and applying the lubricant on the surfaces of the punches and the dies while the lubricant sprayed in the spraying chamber is mixed with the pulsating vibration air, and tabletting the molding material by the punches applied with the lubricant on the surface thereof and the dies applied with the lubricant on the surface thereof.

According to this method, tabletting is continuously executed utilizing the fact that sticking isn't caused. A tablet including compound powdered or granulated which is denaturalized or inactivated when tabletted at high pressure can be produced at industrial production base.

The tablet production method is further characterized in that the following procedures are continuously executed; housing the punches and the dies in the spraying chamber; applying the lubricant on the surfaces of the punches and the dies while the lubricant sprayed in the spraying chamber is mixed with the positive pulsating vibration air; and tabletting the molding material of the punches applied with the lubricant on the surface thereof, and the dies applied with the lubricant on the surface thereof.

According to this method, tabletting is continuously executed utilizing the fact that sticking isn't caused. A tablet including solid dispersion powdered or granulated can be produced at industrial production base.

The tablet production method may be characterized in that tabletting pressure for the molding compound by the punches applied with the lubricant on the surface thereof and the dies applied with the lubricant on the surface thereof is reduced.

Herein "low pressure" means that tabletting pressure is lower comparing with the prior internal lubricant method and the prior external lubricant spraying method. More concretely explained, this tablet production method can produce a tablet having enough practical level hardness even if its tabletting pressure is less than or equal to 1 ton/$cm^2$.

According to this tablet production method, tabletting pressure for molding material is low. Even if the granule included in the tablet is powdered or granular material including compound powdered or granulated which is denaturalized or inactivated when tabletted at high pressure, such material can be tabletted without denaturalizing or deactivating the compound.

Further, even if granule to be included in the tablet is solid dispersion powdered or granulated, such material can be tabletted without destroying the function thereof.

The tablet includes granule containing active agent in diluting agent and lubricant only on the surface thereof and the granule is compound powdered or granulated which is denaturalized or inactivated when tabletted at high pressure.

The tablet has lubricant only on the surface thereof so that delay of tablet disintegration time, which is caused by water repellency of lubricant, isn't happened.

Further, this tablet includes lubricant therein so that it can be tabletted at low tabletting pressure. As a result, compound powdered or granulated which is denaturalized or inactivated when tabletted at high pressure isn't denaturalized or inactivated.

The tablet includes granule containing active agent in diluting agent and lubricant only on the surface thereof, and the granule is solid dispersion powdered or granulated.

Such a tablet is provided with lubricant only on its surface so that disintegration time of the tablet, which may be caused by repellency of lubricant, doesn't delay.

Further, the tablet doesn't include lubricant therein so that it can be tabletted at low pressure and the function of solid dispersion powdered or granulated isn't damaged.

Accordingly, the lubricant amount per tablet is preferably greater than or equal to 0.0001 weight percent and less than or equal to 0.2 weight percent.

Such a tablet is provided with minute amount of lubricant on its surface so that disintegration time delay of the tablet, which may be caused by repellency of lubricant, doesn't happen.

Therefore, when this tablet is used as an uncoated tablet, it becomes a rapidly soluble tablet. It is desirable when a tablet is required to be rapidly disintegrated at an objected place like an intraorally rapidly disintegrable tablet. Further, if the tablet surface is coated with a film which is dissolved at the objective place, the tablet is rapidly dissolved at the objective place when the coated film is dissolved so that such a tablet can be preferably used as a tablet expected to be dissolved at the objective place.

"Anomalous" in this specification means shapes except for round, for example, track (capsule), rugby ball, polygon such as triangle, rectangle, pentagon, and so on, diamond, almond, bombshell, half moon, heart, star, and so on.

Because a tablet has anomalous shape, contained drugs (active agent) can be easily distinguished according to these shapes. As a result, such a tablet doesn't have a fear of medication error.

The tablet is characterized as having a dividing line on the surface thereof.

According to such a tablet, a tablet which is soluble at a desired place and is also dividable can be provided in the market.

BRIEF DESCRIPTION OF DRAWINGS

FIG. 3(*a*) is a schematic section of the external lubricant spraying type tabletting machine according to the present invention. FIG. 3(*b*) is a schematic section around the pulsating vibration air generation means.

FIG. 5(*a*) is a schematic section of an enlarged substantial part of the external lubricant spraying type tabletting machine of the present invention and FIG. 5(*b*) is a schematic sectional view around pulsating vibration air generation means.

FIG. 6(*a*) and FIG. 6(*b*) show positive vibration air respectively.

DISCLOSURE OF THE INVENTION

The tablet production method according to the present invention will be detailed hereinafter referring to the attached drawings.

Here the present invention will be explained when a rotary type tabletting machine is used.

Figure 1:
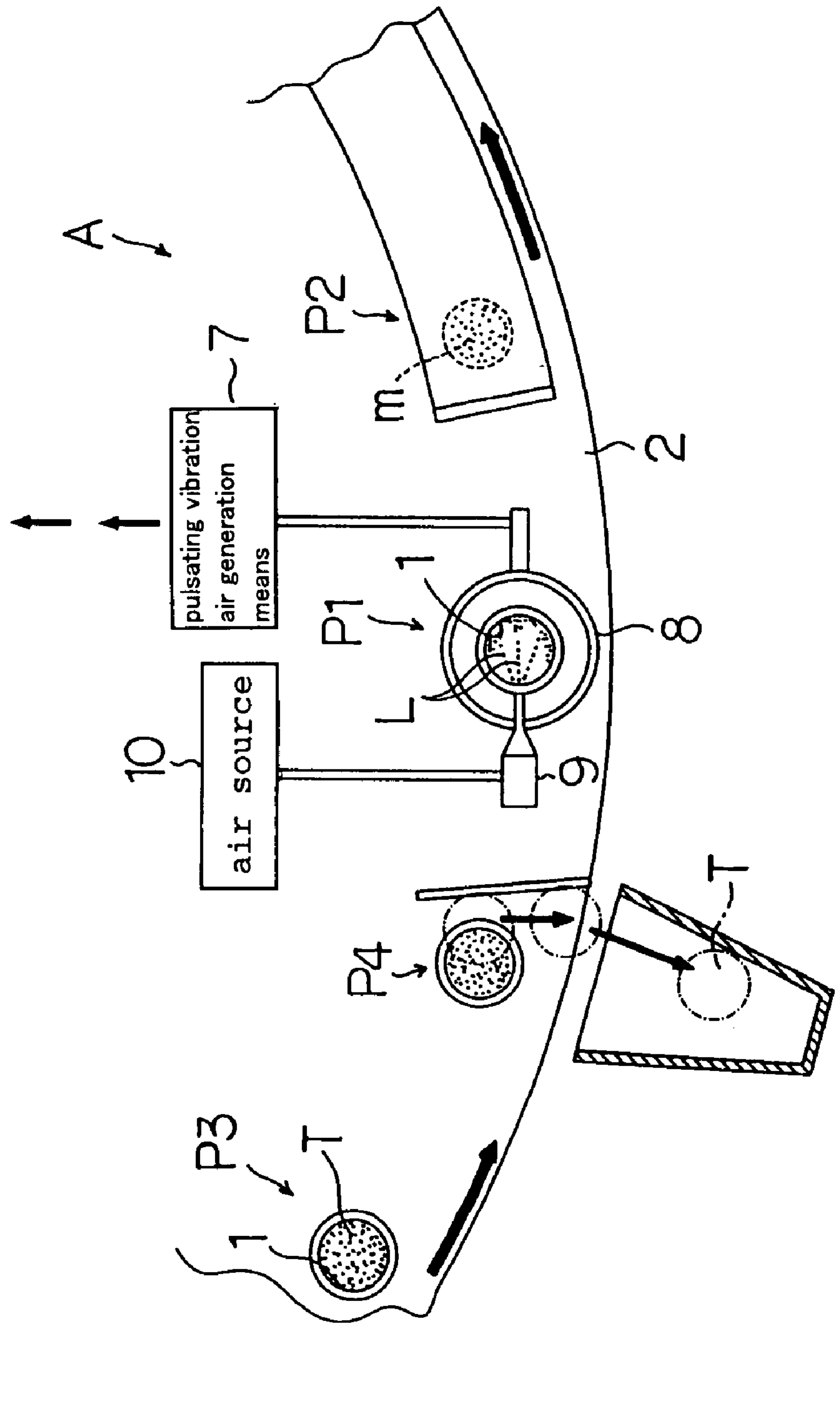
FIG. 1 schematically shows a sectional view of an enlarged substantial part of one embodiment of an external lubricant spraying type tabletting machine used in the tablet production method of the present invention.

FIG. 1 shows schematic construction by enlarging one part around a rotary table of a rotary type tabletting machine used for executing the present invention.

Figure 2:
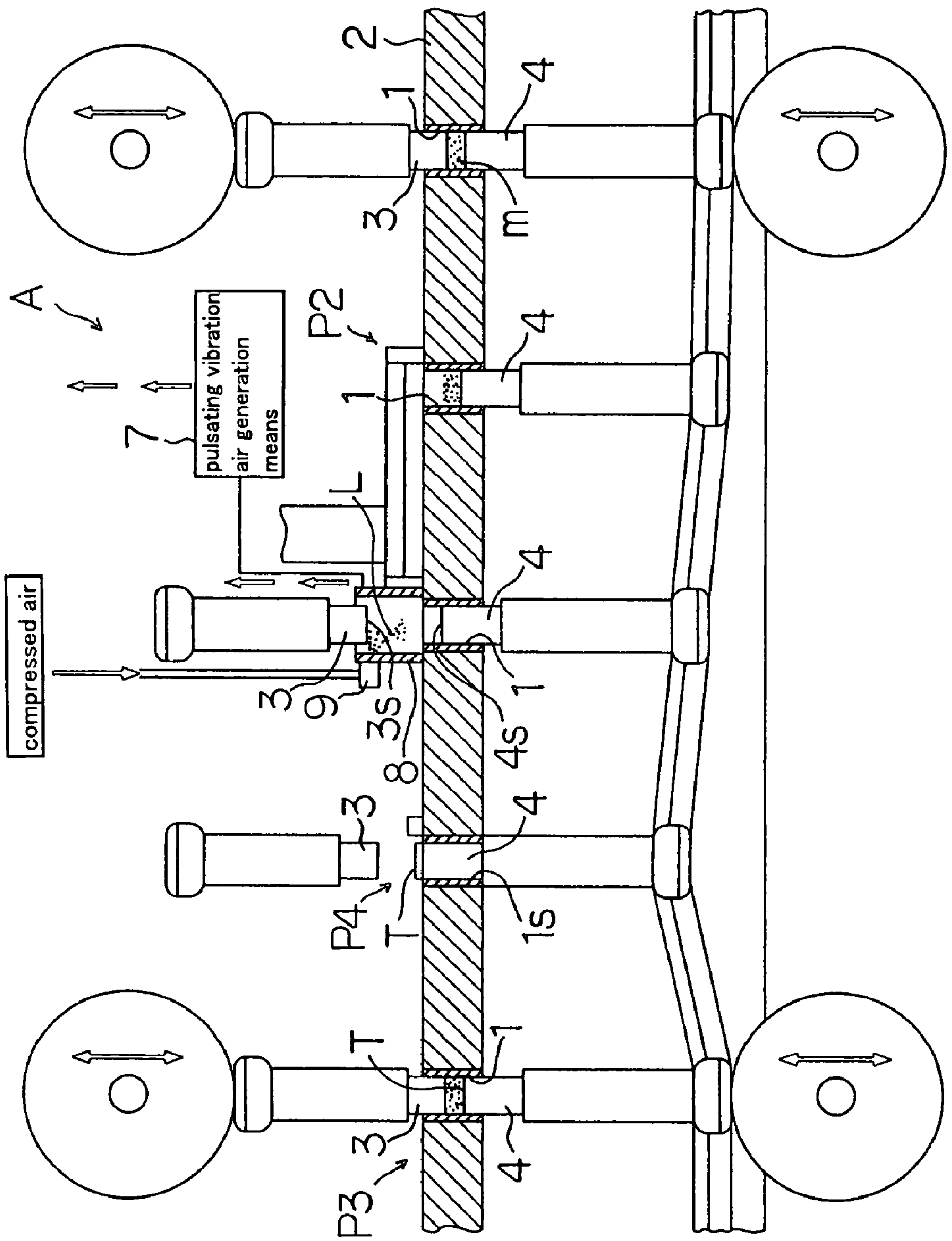
FIG. 2 is a schematic section of the external lubricant spraying type tabletting machine shown in FIG. 1.

FIG. 2 is a schematic section when one part of FIG. 1 around the rotary table is enlarged.

As shown in FIG. 1 and FIG. 2, the rotary type tabletting machine A is comprised of a rotatably provided rotary table 2 having plural dies 1, . . . in circumferential direction, plural upper punches 3, . . . and plural lower punches 4, . . . provided so as to correspond to each dies 1, . . . . A spraying chamber 8 is provided at P1 which is before a point P2 where molding material is charged in the die 1. A pulsating vibration air generation means 7 is connected to the spraying chamber 8 and a spray nozzle 9 for spraying lubricant L is provided in the spraying chamber 8. In this embodiment, an air source 10 such as a cylinder charging compressed air is connected to the spray nozzle 9 and lubricant L is designed to be sprayed from the spray nozzle 9 by the air generated from the source 10.

Next, tablet production procedure using this machine A will be explained.

The rotary table 2 is rotated at a fixed speed, pulsating vibration air is generated in the spraying chamber 8 by driving the pulsating vibration air generation means 7 when the die 1 comes to the point P1 where the spraying chamber 8 is provided according to rotation of the rotary table 2, lubricant L is simultaneously sprayed from the spray nozzle 9, and lubricant L is applied on an inner wall is of the die 1, a lower surface 3*s* of the upper punch 3, and an upper surface 4*s* of the lower punch 4.

Then, molding material m is charged in the die 1 which comes to the point P2 for charging molding material m in the die 1 accompanied with rotation of the rotary table 2 and extra molding material m is removed. Thereafter, when the die 1 charged with molding material m comes to a point P3 for compressing molding material m, molding material m in the die 1 is compressed to produce a tablet by means of the upper punch 3 of which lower surface 3*s* is applied with lubricant L and the lower punch 4 of which upper surface 4s is applied with lubricant L. Further, when the die 1 comes to a point P4, a tablet T is discharged from the die 1 so that the tablet T is produced.

Figure 3:
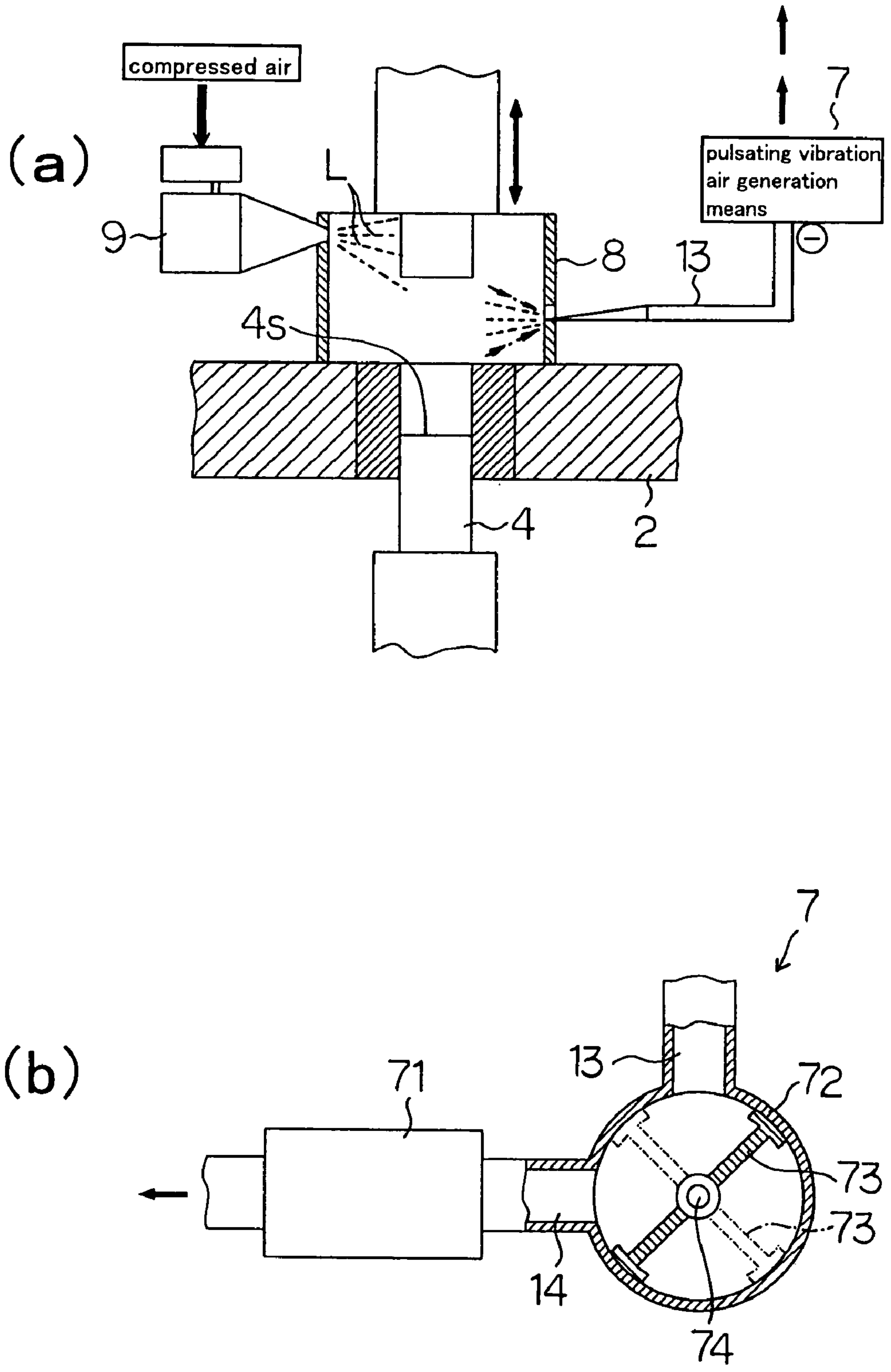
FIG. 3 schematically shows a substantial part of the external lubricant spraying type tabletting machine shown in FIG. 1.

FIG. 3(*a*) shows schematic construction around the spraying chamber 8 and FIG. 3(*b*) illustrates construction by an example of pulsating vibration air generation means 7.

In this example, the pulsating vibration air generation means 7 is connected to the spraying chamber 8 via a conduit 13.

In FIG. 3(*b*) the numeral 71 shows a blower, 72 shows a cylindrical tube, 73 shows a valve element provided rotatably around a rotary axis 74 so as to divide inside of the tube 72 into two parts. The conduit 13 and a conduit 14 coupled to the blower 71 are connected at a given place of the side of the tube 72. The valve element 73 is designed to be rotated at a desired rotational velocity by means of a valve rotation control means (not shown).

When the blower 71 is rotated at a given rotation number and the valve element 73 is also rotated at a given rotation number, the spraying chamber 8 and the blower 71 are connected as the valve element 73 is positioned at a place shown by a solid line in the figure. When the valve element 73 is positioned at a place shown by a dotted line, the spraying chamber 8 and the blower 71 are blocked off by the valve element 73. Accordingly, pulsating vibration air with its peak at atmospheric pressure and its valley at negative pressure shown in FIG. 4(*a*) or pulsating vibration air with its peak and valley at negative pressure shown in FIG. 4(*b*) can be produced in the spraying chamber 8.

Here "negative pressure" means that the pressure in the spraying chamber 8 is lower than outside pressure (atmospheric pressure).

According to this tablet production method, because lubricant L isn't included in the molding material m, produced tablet can obtain practical hardness even if tabletting pressure is less than or equal to 1 ton/cm$^2$. Therefore, this method is suitable for producing a tablet including compound which is denaturalized or inactivated when tabletted at high pressure and a tablet including solid dispersion powdered or granulated.

Figure 4:
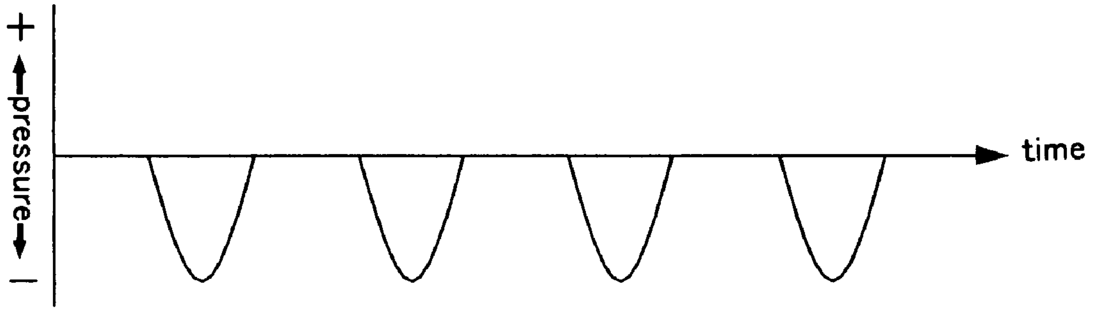
FIG. 4 explains a concrete example of pulsating vibration air, FIG. 4(*a*) and FIG. 4(*b*) show negative pulsating vibration air respectively.
Figure 4:
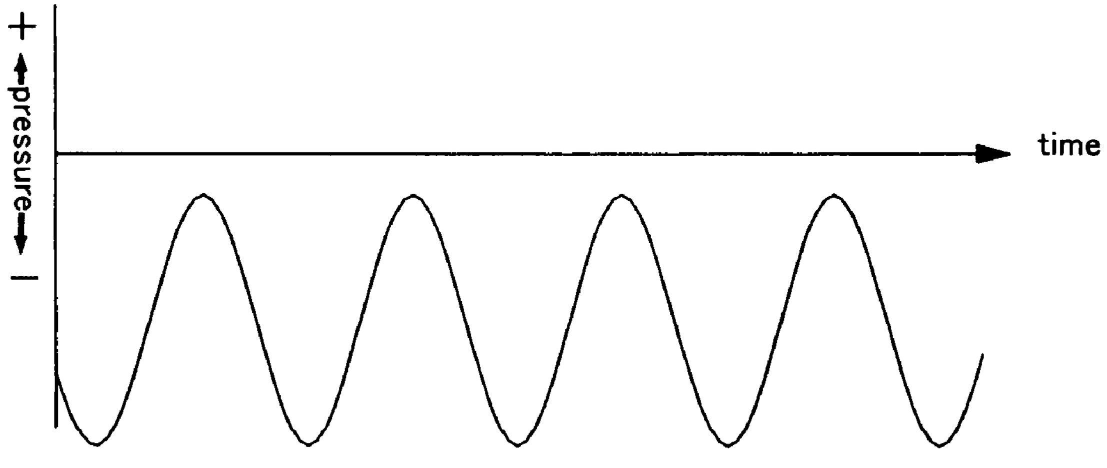

When lubricant L is sprayed from the spray nozzle 9 while generating pulsating vibration air shown in FIG. 4(*a*) or FIG. 4(*b*), sprayed lubricant L is diffused by the pulsating vibration air and attaches on the inner wall 1s of the die 1, the lower surface 3s of the upper punch 3 and the upper surface 4s of the lower punch 4 both of which are provided so as to correspond to the die 1 housed in the spraying chamber 8.

According to this tablet production method, as lubricant L can be uniformly applied on the inner wall 1s of the die 1, the lower surface 3s of the upper punch 3, and the upper surface 4s of the lower punch 4, molding material m can be prevented from adhering on the die 1, the upper punch 3, and the lower punch 4 of the tabletting machine A even if the amount of lubricant L sprayed in the spraying chamber 8 is only a little.

Utilizing this, if the spray amount of lubricant L to be sprayed in the spraying chamber 8 is controlled to be greater than or equal to 0.0001 weight % and less than or equal to 0.2 weight % per the weight of tablet, a part of lubricant L attached on the inner wall is of the die 1, the lower surface 3s of the upper punch 3, and the upper surface 4s of the lower punch 4 is slightly attached only on the surface of the produced tablet T so that the tablet T without including lubricant L therein can be produced.

As the result, the used amount of lubricant L for the tablet T is remarkably small comparing with the tablet produced by the prior production method. Therefore, a problem, which has been found in the prior tablet, wherein disintegration time of tablet delays because of water repellency of lubricant L is never happened.

Accordingly, if the tablet T produced according to the above-mentioned method is used as an uncoated tablet, it becomes a rapidly soluble tablet and is suitable as a tablet which is required to be rapidly disintegrated at an objected part like an intraorally rapidly disintegrable tablet.

If a film coat which can be melted at an objective part is executed on the surface of the tablet, the tablet is rapidly dissolved at an objective part when the film coat is melted. Consequently, a tablet which can be dissolved at an objective part can be produced.

In this embodiment, the system shown in FIG. 3(*b*) is used as a pulsating vibration air generation means 7, however, it is only an example and any kinds of system can be used as the pulsating vibration air generation means 7. For example, the blower 71 may be connected to the end of the conduit 13, a solenoid valve may be provided in the middle of the conduit 13 for opening and closing the conduit 13, the blower 71 may be rotated at a given rotation number so as to suck air in the spraying chamber 8, and the conduit 13 may be opened or closed at a prescribed period by the solenoid valve. Otherwise the blower 71 may be connected to the end of the conduit 13, the blower 71 may be rotated fast or slowly at a given period, and air in the spraying chamber 8 may be sucked strongly and weakly.

Figure 5:
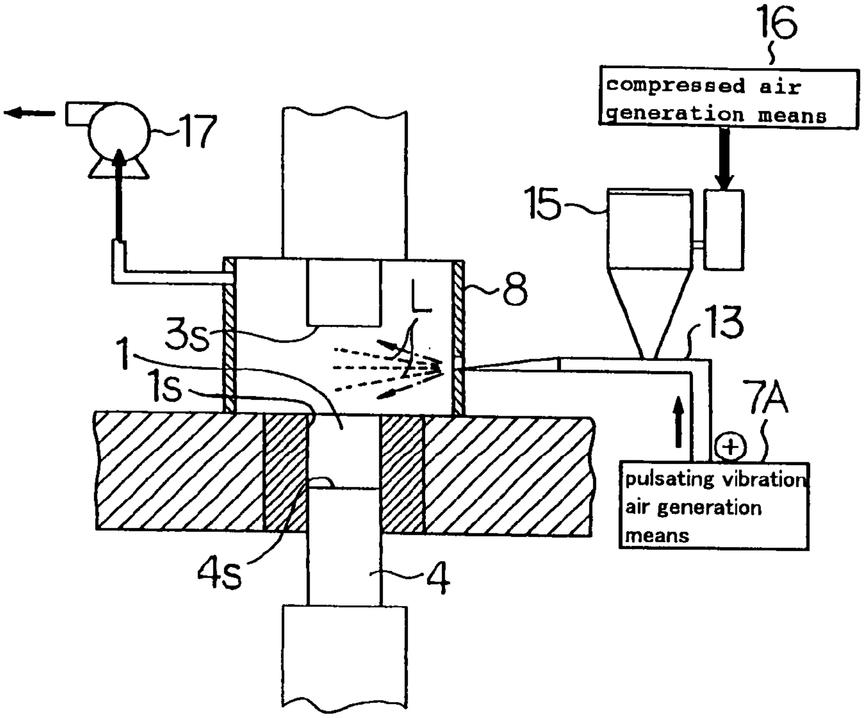
FIG. 5 schematically shows other embodiment of the external lubricant spraying type tabletting machine used for the tablet production method of the present invention.
Figure 5:
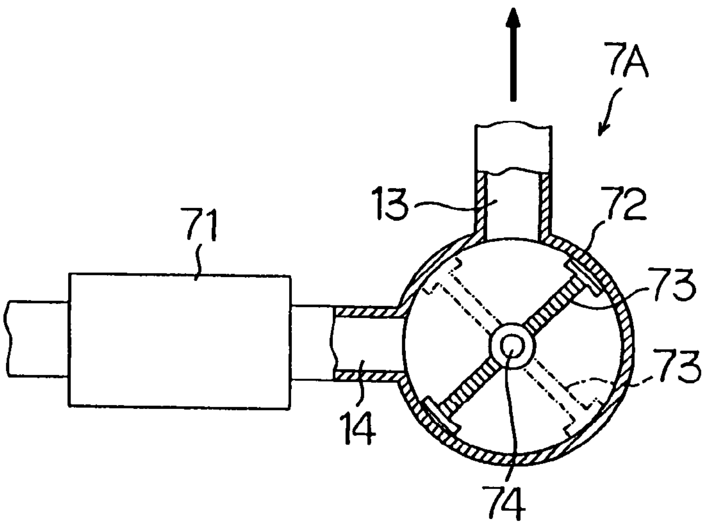

Also in the above-mentioned embodiment, the pulsating vibration air shown in FIG. 4(*a*) or FIG. 4(*b*) is generated. The system shown in FIG. 5 may be constructed and the pulsating vibration air shown in FIG. 6(*a*) or FIG. 6(*b*) may be generated in the spraying chamber 8. Namely, in the embodiment shown in FIG. 5, a pulsating vibration air generation means 7A is connected to the end of the conduit 13, a hopper 15 storing lubricant L is connected in midstream of the conduit 13, and a compressed air generation means 16 such as a cylinder charging compressed air is connected to the hopper 15 as shown in FIG. 5(*a*). The numeral 17 in FIG. 5(*a*) shows a blower provided if required. When the blower 17 is driven, air in the spraying chamber 8 is sucked and pulsating vibration air supplied in the spraying chamber 8 and lubricant L are induced to be discharged from the spraying chamber 8.

As shown in FIG. 5(*b*), the pulsating vibration air generation means 7A is provided with the blower 71, the cylindrical tube 72 connected to the conduit 13 between the blower 71 and the hopper 15, and the valve element 73 which is rotatable around the rotary axis 74 in the tube 72 and is designed to divide the inside of the tube 72 into two parts. The conduit 13 and the conduit 14 coupled to the blower 71 are connected to the side of the tube 72. The valve element 73 is constructed so as to be rotated at a desired rotational velocity by means of a valve rotation control means (not shown).

Figure 6:
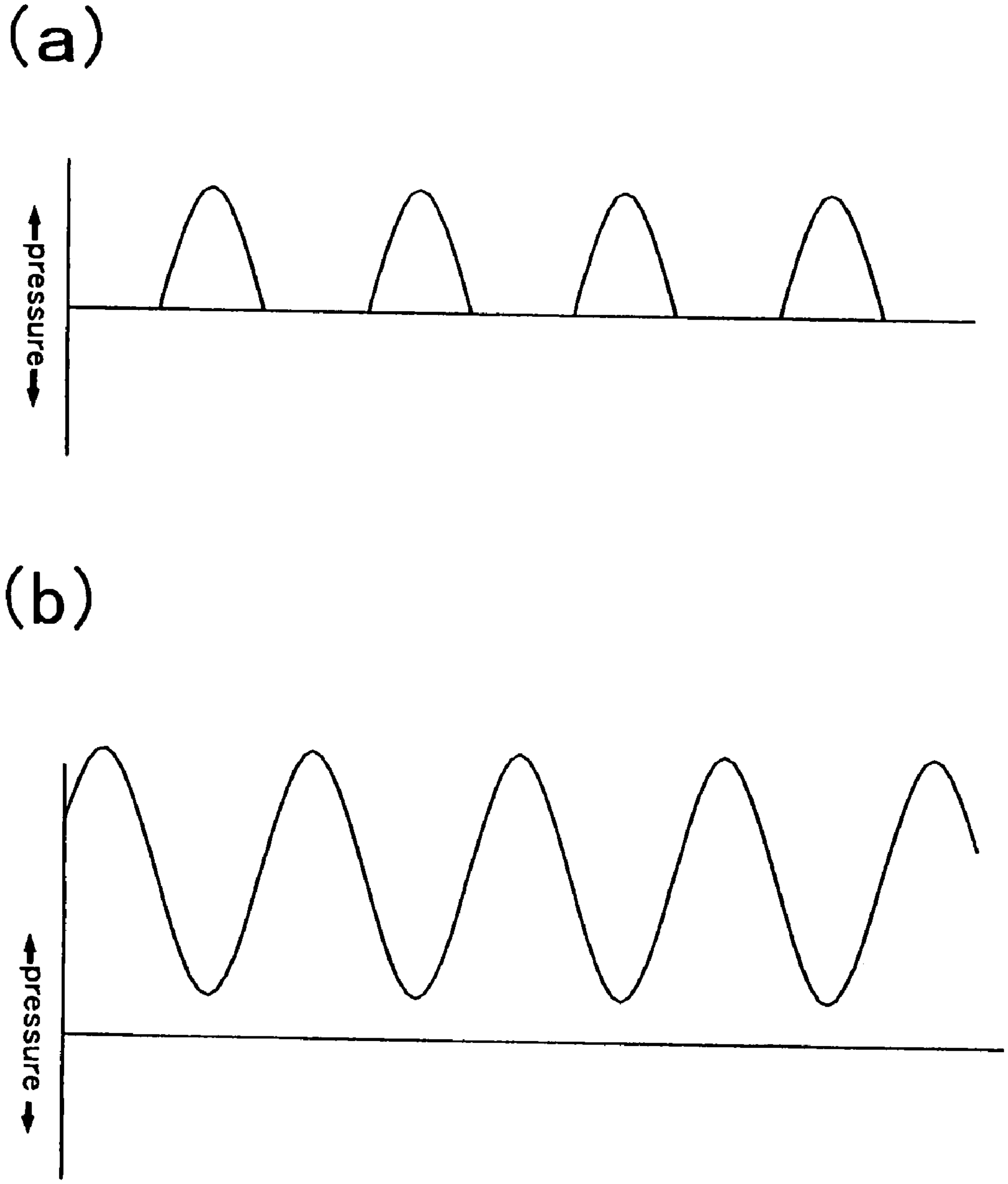
FIG. 6 explains a concrete example of pulsating vibration air.

When the blower 71 is rotated at a given rotation number to send air to the spraying chamber 8 and the valve element 73 is also rotated at a given rotational velocity, the spraying chamber 8 and the blower 71 are connected when the valve element 73 is located at the place shown as a slid line in the figure. When the valve element 73 is located at a dotted line, the spraying chamber 8 and the blower 71 are blocked off by the valve element 73. Accordingly pulsating vibration air with its peak at positive pressure and its valley at atmospheric pressure as shown in FIG. 6(*a*) is generated in the spraying chamber 8. Otherwise, pulsating vibration air with its peak and valley at positive pressure as shown in FIG. 6(*b*)

may be generated in the spraying chamber 8. While keeping this condition, the compressed air generation means 16 may be driven to feed lubricant L contained in the hopper 15 to the conduit 13 and a fixed amount of lubricant L may be supplied in the spraying chamber 8 together with the current of pulsating vibration air.

Here positive pressure means that the pressure in the spraying chamber 8 is higher than the pressure outside of the spraying chamber 8 (atmospheric pressure).

Otherwise, the blower 71 may be provided at the end of the conduit 13, the solenoid valve for opening and closing the conduit 13 may be also provided in the midstream of the conduit 13, the blower 71 may be rotated at a given rotation number to feed air in the spraying chamber 8, the conduit 13 may be opened and closed periodically, then pulsating vibration air may be generated in the spraying chamber 8 and the conduit 13. While keeping such a condition, the compression air generation means 16 may be driven to feed lubricant L contained in the hopper 15 to the conduit 13 and a fixed amount of lubricant L is supplied in the spraying chamber 8 together with the current of pulsating vibration air. On the other hand, the blower 71 may be connected at the end of the conduit 13, the blower 71 may be rotated fast or slowly at a given period so as to feed air strongly or weekly in the spraying chamber 8, and pulsating vibration air may be generated in the spraying chamber 8 and the conduit 13. While keeping this condition, the compression air generation means 16 may be driven so as to feed lubricant L contained in the hopper 15 to the conduit 13 and a fixed amount of lubricant L may be supplied in the spraying chamber 8 together with the current of pulsating vibration air.

The present invention will be further explained based on concrete experimental data.

(Experiment 1)

Here an example of producing tablet including powdered or granular compound which is denaturalized or inactivated when tabletted at high pressure is shown.

Water solution of 15 w/v % lactose was mixed with water solution of 10 w/v % serrapeptase in a ratio of 10 g serrapeptase to 50 g lactose. The mixture was frozen and dried under the condition wherein initial temperature at −55° C. and pressure at $10^{-3}$ mmHg; final temperature after 27 hours at +60° C. and pressure at $10^{-1}$ mmHg and then mixed, kneaded, dried, and sized. The powdered or granular material (average particle size: 60 $\mu$m) of which prescription is shown in table 1 is prepared.

TABLE 1

| combined ingredient | Prescription (mg) |
|---|---|
| serrapeptase | 5 mg |
| lactose | 87 mg |
| cornstarch | 37.5 mg |
| isopropanol | 0.015 ml |

Then using the rotary tabletting machine A provided with the pulsating vibration air generation means 7 shown in FIG. 1, material was continuously tabletted by means of 7 mm diameter die and punch set at a rotational velocity which rotates the rotary table 2 at 30 times per minute so as to produce the sized granulated material of 130 mg/tablet.

Magnesium stearate was used as lubricant and the used amount of magnesium stearate sprayed in the spraying chamber 8 was controlled such that weight % of the lubricant included per a produced tablet becomes 0.03 weight %.

HATA HT-X20 by Hata Seisakusho Co., Ltd. was used as a main body of the tabletting machine A.

When the rotary type tabletting machine A provided with the pulsating vibration air generation means 7 shown in FIG. 1 was used, it was found that the produced tablet has practical hardness at a tabletting pressure of 0.7 ton/$cm^2$.

The condition of pulsating vibration air isn't specifically limited. However, in this experiment, the period of pulsating vibration air was greater than or equal to 1 Hz and less than or equal to 10 Hz, its valley became 15%–5% lower than atmospheric pressure and also its peak became almost the same as or a little lower than atmospheric pressure.

(Comparison 1)

Magnesium stearate was added as lubricant for the powdered or granular material used in the experiment 1 as shown in table 1 in a ration of 0.8 weight % for the entire amount of a tablet. After they were well mixed by a V type mixer, they were continuously tabletted by an internal lubricant method at a speed of rotating the rotary table at 30 times per minute by means of a set of 7 mm punch and die so as to produce the material into a 130 mg tablet.

HATA HT-X20 by Hata Seisakusho Co., Ltd. was used as the tabletting machine A.

In this case it was found that the produced tablet didn't have practical hardness at a tabletting pressure of 0.7 ton/c$m^2$.

(Comparison 2)

The powdered or granular material used in the experiment 1 as shown in table 1 was tabletted by means of a set of 7 mm punch and die so as to produce a 130 mg tablet. Stearate magnesium was applied on the surfaces of the punch and die according to the method described in JP-B-41-11273 so that the weight % of lubricant became 0.03 weight % per a produced tablet. Then the material was continuously tabletted at a speed of rotating the rotary table 30 times per minute.

HATA HT-X20 by Hata Seisakusho Co., Ltd. was used as the tabletting machine A.

Next, disintegration test according to Japanese Pharmacopoeia was executed for three kinds of tablets produced according to the experiment 1, the comparison 1, and the comparison 2 at a given test number (N=5).

The result is shown in Table 2.

TABLE 2

| | Tabletting Pressure (ton/$cm^2$) | hardness (kg) | disintegration time: average measurement (standard variation) | disintegration time: actual measurement |
|---|---|---|---|---|
| experiment 1 | 0.7 | 7 | 3.0 (±0.2) | 3.0<br>2.7<br>2.9<br>3.2<br>3.1 |
| comparison 1 | 0.7 | 4 | 7.2 (±0.9) | 7.2<br>7.8<br>8.3<br>6.4<br>6.2 |
| comparison 2 | 0.7 | 7 | 4.0 (±0.6) | 4.1<br>3.5<br>3.3<br>4.8<br>4.5 |

According to the table 2, it was found that the experiment had high hardness comparing with the comparison 1 and had ort disintegration time comparing with the comparison 1 and And also its disintegration time doesn't widely vary.

(Comparison 3)

Magnesium stearate was added as lubricant for the powdered or granular material used in the experiment 1 as shown in the table 1 in a ratio of 0.8 weight % for the entire amount of a tablet. After they were well mixed by a V type mixer, they were continuously tabletted by an internal lubricant method at a speed of rotating the rotary table 30 times per minute by means of a set of 7 mm punch and die so as to produce a 130 mg tablet.

In this case a tabletting pressure was 1.3 ton/cm$^2$ so that produced tablet has practical hardness.

Next, residual ratio of serrapeptase was measured for the experiment 1, the comparison 1, and the comparison 2. The result was the experiment 1>the comparison 1>and the comparison 2.

Concretely explained, after the tablet including serrapeptase obtained in the experiment 1, the comparison 1, and the comparison 2 were preserved at 40° C. for three months, residual ratio of serrapeptase was measured. The residual ratio of the experiment 1 was 98.8%, that of the comparison 1 was 90.7%, and that of the comparison 2 was 87.9%. Accordingly, the tablet including serrapeptase produced according to the present invention had higher stability comparing with the tablet including serrapeptase produced according to the prior invention.

For each experiment 1, comparisons 1–3, material was continuously tabletted for 5 hours and produced tablet was sampled with time. Time which didn't cause sticking was measured by smoothness of produced tablet surface. In the experiment 1, sticking wasn't happened after 5 hours. However, in the comparison 1 and 3 sticking was happened after 1 hour and in the experiment 2 sticking was happened after 2 hours.

Based on the above-mentioned results, a tablet produced according to the present invention can achieve practical hardness even if tablet is produced at a tabletting pressure less than or equal to 1 ton/cm$^2$. Therefore, when the present tablet production method is applied for producing tablet including drugs having inferior stability (for example activity is deteriorated), the present invention can heighten stability of drugs included in tablet comparing with the tablet produced according to the prior art (for example there is no problem such as deteriorating activity of drugs included in tablet).

Therefore, for example, when the tablet including many drugs as shown in tables 3–5 is produced, the tablet production method according to the present invention is effective.

TABLE 3

| | |
|---|---|
| 1.Antipyretics, Analgesics, Antiinflammatory agents | Indometacin, Dicrofenac sodium, Ibuprofen, Asprin, Dexamethasone, Prednisolone, Loxoprofen sodium, Ketoprofen, Serrapeptase, Lysozyme Chloride, Streptokinaze, Salicylamide |
| 2.Antacid, Antiulcers | Famotidine, Sucralfate, Cimetidine, Aceglutamide aluminium, Dried aluminium hydroxide gal, Sodium bicarbonate, Diastase, Sodium copper chlorophyllin, L-glutamine, Sodium alginate |
| 3.Antihypertensives, Cardiovascular agents | Benidipine hydrochloride, nifedipine, nicardipine hydrochloride, amlodipine besylate |
| 4.Antibiotics | Amoxicillin, Ampicillin, Minocycline hydrochloride, |

TABLE 3-continued

| | |
|---|---|
| 5.Antitussives, Antiasthma agents, Bronchodialators | Theophylline, Methlyephedrine hydrochloride, Sodium cromoglicate, Salbutamol sulfate, Codeine phosphate |
| 6.Diuretics | Furosemide, Chlorothiazide, Spironolactone |
| 7.Tranquilizers | Diazepam, Chlorpromazine, Haloperidol, Bromperidol, Risperidone |
| 8.Antipodagrics | Allopurinol, Probenecid |
| 9.Anticoagulants | Warfarin, Heparin sodium, Alteplase, Urokinase, tisokinase |
| 10.Blood coagulants | Blood coagulant factor VIII, Active prothombine complex |
| 11.Erythropoietins | Epoetin β, Epoetin α |
| 12.Hypolipidemics | Pravastatin sodium, Simvastatin, Bezafibrate, Tocopherol nicotinate, Dextran sulfate sodium |
| 13.Cerebral vasodilators, Peripheral vasodilators | Nicergol, Ibudilast, Citicoline, Flunarizine hydrochloride |
| 14.Calcitonins | Elcatonin, Salmon calcitonin(synthetic) |
| 15.Anticonvulsants | Phenytoin, Sodium propyl valerate, Carbamazepine, Zonisamide |

TABLE 4

| | |
|---|---|
| 16.Antiemetics | Metoclopramide, Donpridone, Cisapride |
| 17.Expectorants | Bromhexine hydrochloride, Carbocisteine, Cysteine ethylester hydrochloride, Ambroxol hydrochloride |
| 18.Antidiabetes | Glibenclamide, Tolbutamide, Insulin, Glucagon - like insulintropic peptide |
| 19.Cardio vascular agents | Ubidecarenon, ATP-2 sodium, Nitroglycerin, Isosorbide didinirate |
| 20.Vitamins | Vitamin A, Vitamin B, Vitamin C, Vitamin D, Folic acid |
| 21.Antipollakisurias Antiduretic hormones | Flavoxate hydrochloride, Oxybutynin hydrochloride, Desmopressin acetate, Vasopressin |
| 22.Ace inhibitors | Enalapril maleate, Alacepril |
| 23.Antiparkinsonism | Droxidopa, Pergolide mesilate, levodopa, carbidopa |
| 24.Digestives | Pancreatic digestive enzyme, Sanactase combined drug, Gastric mucosa extraction drug, Tilactase |
| 25.Anticancer agents | Tegaful, Fluorouracil, Doxifluridine, Methotrexate, Etoposide, Vindesine sulfate, Epirubicin hydrochloride, L-asparaginase, Leuprorelin acetate, Goserelin acetate, Chlormadinone acetate, Tamoxifen citrate, Filgrastim, Lenograstim, nartograstim, Lentinan, Interferon |
| 26.Immunosuppressor | Cyclosporin, Mizoribine, Immunoglobulin |
| 27.Anesthesias | Lidocaine hydrochloride, Procaine hydrochloride, morphine sulfate, Buprenorphine hydrochloride, Pentazocine, Fentanyl |
| 28.Sedatives | Brotizolam, Triazolam, Flunitrazepam, Flurazepam hydrochloride |
| 29.Nootropics | Idebenone, Propentofylline, Indeloxazine hydrochloride, Bifemelane hydrochloride, |

TABLE 5

| | |
|---|---|
| 30.Antiallergies | Beclometasondipropionat, Ketotifen fumarate, Amlexanox, Terfenadine, Azelastin hydrochloride, Tranist, Olopatadine, Oxatomide, Epinastine hydrochloride, Astemizole |
| 31.Diagnostics, Other therepeutic agents | [$^{13}$C]Urea, Glucagon, Partially hydolyzed starch, Prostaglandin, Leukotriene, Thromboxan A2, Platelet activating factors, insulinnoid growth factors, Neurone growth factors, Epidermal growth factors, Vascular endothelial growth factors, Ribonucleic acid, Deoxyribonucleic acid, Oligonucleoside, Ttrehalose, Dextran, |

TABLE 5-continued

| |
|---|
| Chitin, Acacia, Agar, Chondroitin sulfuric acid, Hyaluronic acid, Cyclodextrin, β glucan, Trypsin, Chymotrypsin, Pepsin, Aprotinin, Bestatin, Mumpsvaccine, Poliovaccine |

Further, it was found that sticking and so on were hardly caused when tabletting.

(Experiment 2)

Here an example of producing a tablet including solid dispersion powdered or granulated.

2500 g of hydroxypropylmethylcellulose acetate succinate (brand name: A coat, AS-MP, Shinetsu Kagaku Kogyo Co., Ltd.) was mixed with 500 g of original powder (average particle size 60 μm) made by grinding donperidone. Thereafter, processing treatment was executed by means of a dual axis extruder equipped with dies of 4 mmø×2 caliber (KEX-25: Kurimoto Tekkosho Co., Ltd.) at 100° C. barrel temperature at extruding speed of 200 rpm while adding a little water, thereby solid dispersion was obtained.

Thus obtained solid dispersion was minutely ground by a sample mill (type: AP-S, Hosokawa Tekkosho Co., Ltd.).

Next, such solid dispersion was tabletted by a tabletting machine with an external lubricant spraying means A as follows. The punches 3, 4 and the die 1 were housed in the spraying chamber 8, magnesium stearate was applied as lubricant L on the surfaces of 3*s*, 4*s* of the punches 3, 4 and the surface is of the die 1 by generating pulsating vibration air as shown in FIG. 4(*a*) in the spraying chamber 8. The substance was continuously tabletted by means of the punches 3, 4 and the die 1 on which surfaces 3*s*, 4*s*, 1*s* were applied with magnesium stearate at a speed of rotating the rotary table at 30 times per minute.

The conditions of pulsating vibration air isn't limited. However in this example, period of pulsating vibration air was more than or equal to 1 Hz and less than or equal to 10 Hz, the valley thereof was set at about 10% lower than atmospheric pressure, and the peak thereof was equal to or a little less than atmospheric pressure.

Next, solubility test of thus obtained tablet of solid dispersion and powder X-ray diffraction test (250 mesh passing) were executed.

(Comparison 4)

2500 g of hydroxypropylmethylcellulose acetate succinate (brand name: A coat, AS-MP, Shinetsu Kagaku Kogyo Co., Ltd.) was mixed with 500 g of original powder (average particle size 60 μm) made by grinding donperidone. Thereafter, processing treatment was executed by means of a dual axis extruder equipped with dies of 4 mmø×2 caliber (KEX-25: Kurimot Tekkosho Co., Ltd.) at 100° C. barrel temperature at extruding speed of 200 rpm while adding a little water, thereby solid dispersion was obtained.

Thus obtained solid dispersion was minutely ground by a sample mill (type: AP-S, Hosokawa Tekkosho Co., Ltd.) and solubility test of thus obtained minute particle and powder X-ray diffraction test (250 mesh passing) were executed.

As a result, the experiment 2 and the comparison 4 showed almost the same solubility and it was found that crystal peak of donperidone of both cases were disappeared.

For the experiment 2 and the comparison 4, material was continuously tabletted for 5 hours and tablets were sampled with time, then time without happening sticking was measured by smoothness of the produced tablets. Sticking wasn't seen after 5 hours in the experiment 2, however in the comparison 4, sticking was already seen after 1 hours.

Several kinds of solid dispersion was produced for the several drugs shown in the tables 3–5 by means of a dual axis type extruder and similar tests as the experiment 2 and the comparison 4 were executed.

The punches 3, 4 and the die 1 were housed in the spraying chamber 8, magnesium stearate was applied as lubricant L on the surfaces of 3*s*, 4*s* of the punches 3, 4 and the surface is of the die 1 by generating pulsating vibration air as shown in FIG. 4(*a*) in the spraying chamber 8. The substance was continuously tabletted by means of the punches 3, 4 and the die 1 on which surfaces 3*s*, 4*s*, is were applied with magnesium stearate at a speed of rotating the rotary table at 30 times per minute. It was found that thus obtained tablet and minute particles obtained by grinding the solid dispersion by a sample mill had almost the same solubility and crystal peak of both of them were disappeared.

According to the above-mentioned results, it was found that the tablet production method according to the present invention could be preferably used for producing a tablet of solid dispersion.

Next, several anomalous tablets shown in FIGS. 7–11 were produced similar to the experiment 1, 2, however a punch and a die comprising a female mold of tablet.

Figure 7:
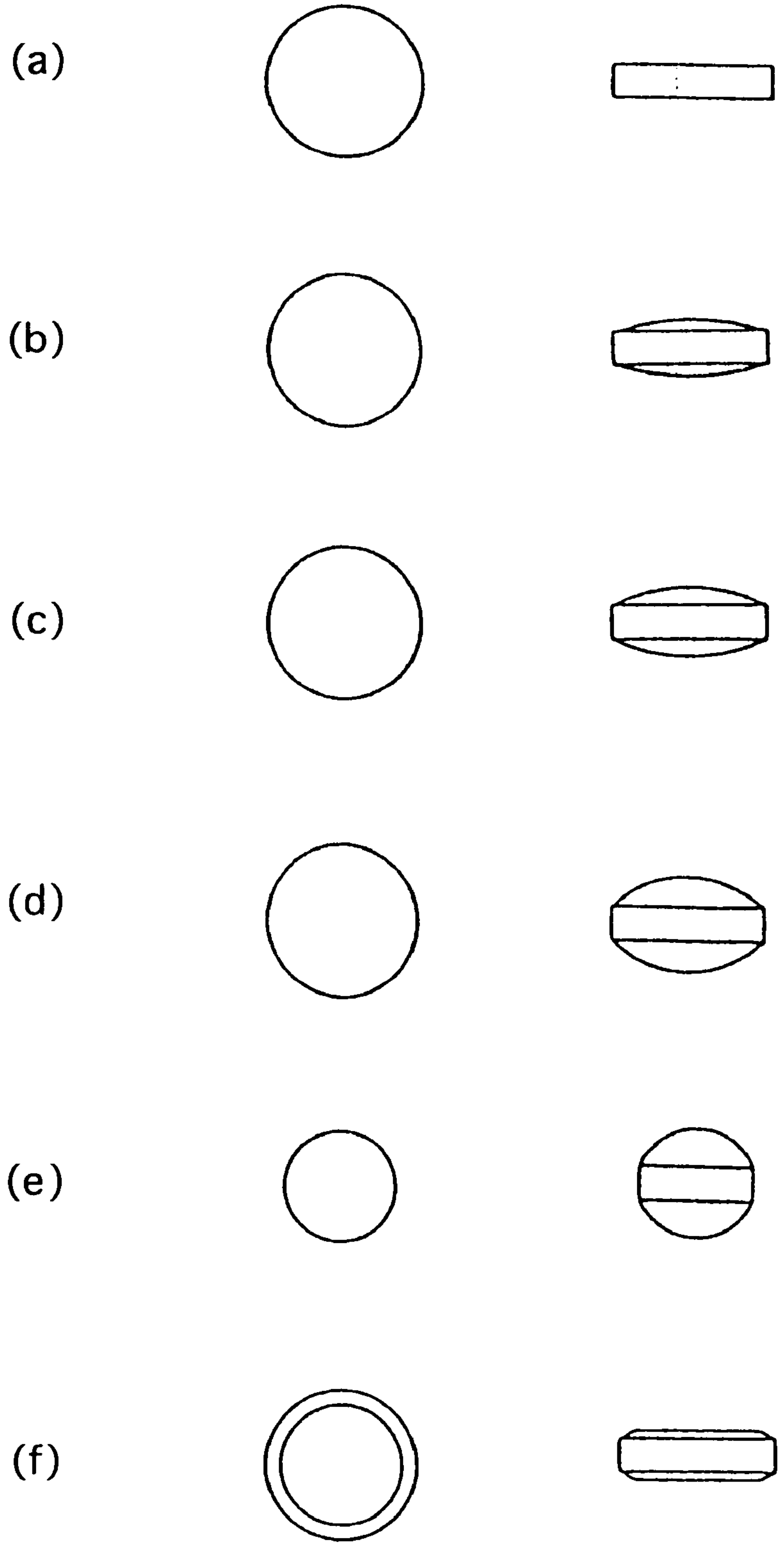
FIG. 7 schematically explains many kinds of tablets produced in experiments. A schematic plane view of each tablet is shown at left and its schematic side view is shown at right.

The tablet in FIG. 7(*a*) shows a circular tablet generally called flat plain, the tablet in FIG. 7(*b*) shows a circular tablet generally called shallow concave plain, the tablet in FIG. 7(*c*) shows a circular tablet generally called normal concave plain, the tablet in FIG. 7(*d*) shows a circular tablet generally called deep concave plain, tablet in FIG. 7(*e*) shows a circular tablet generally called ball or pill, tablet in FIG. 7(*f*) shows a circular tablet generally called flat beveled edge.

Figure 8:
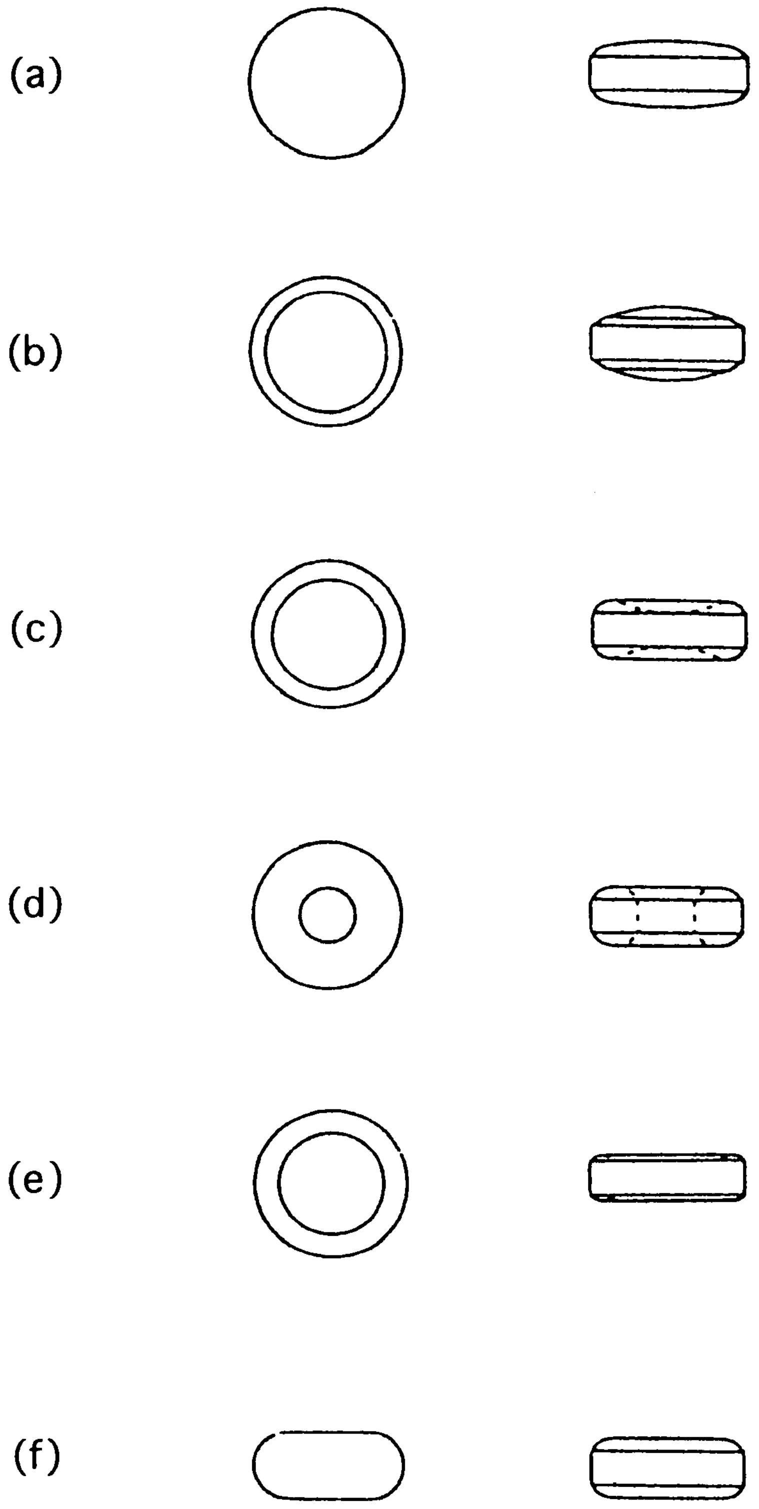
FIG. 8 schematically explains many kinds of tablets produced in experiments. A schematic plane view of each tablet is shown at left and its schematic side view is shown at right.

The tablet in FIG. 8(*a*) shows a circular tablet generally called double radius, the tablet in FIG. 8(*b*) shows a circular tablet generally called bevel and concave, the tablet in FIG. (8*c*) shows a circular tablet generally called ring, the tablet in FIG. 8(*e*) shows a a circular tablet generally called rim, and the tablet in FIG. 8(*f*) shows a capsule type tablet generally called capsule.

Figure 9:
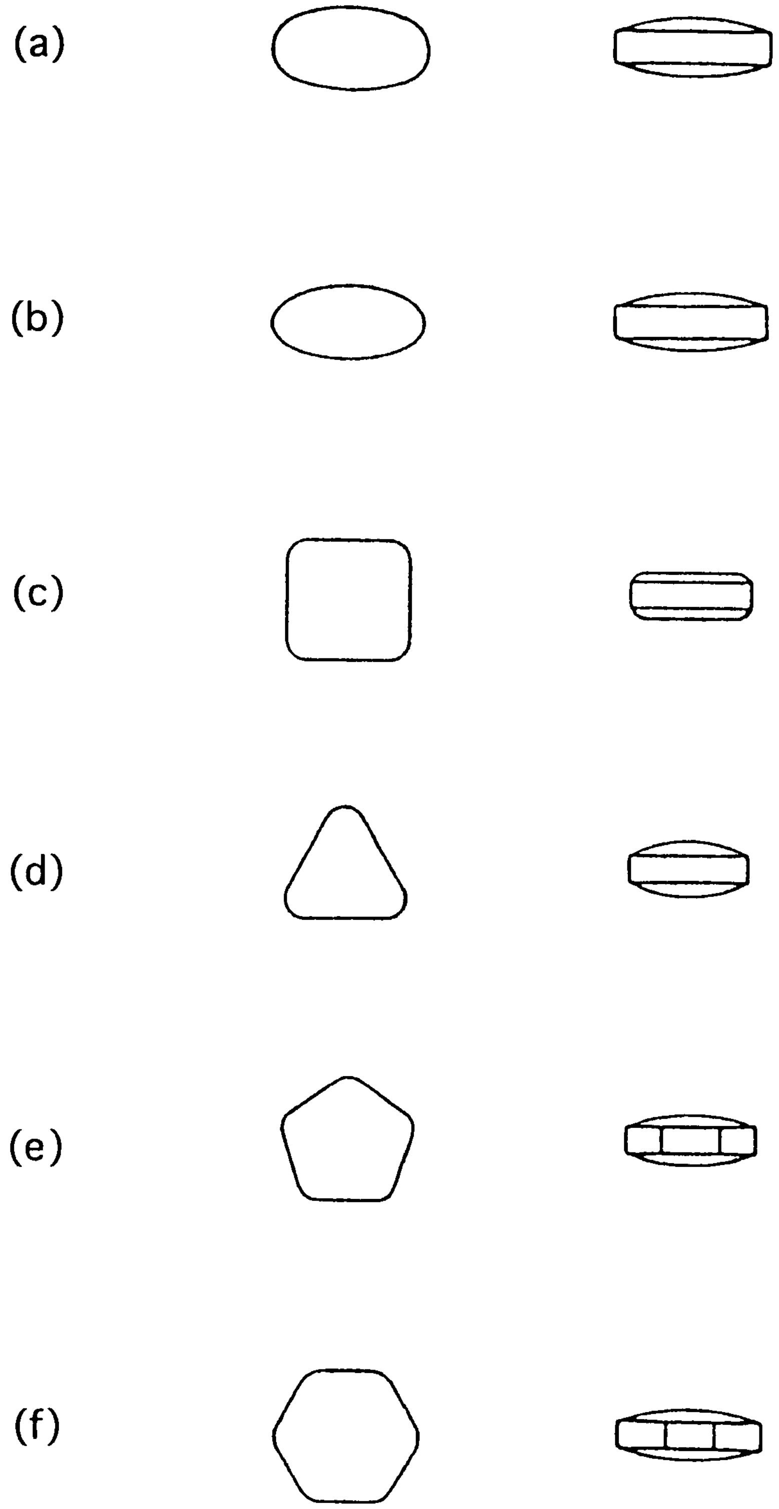
FIG. 9 schematically explains many kinds of tablets produced in experiments. A schematic plane view of each tablet is shown at left and its schematic side view is shown at right.

The tablet in FIG. 9(*a*) shows a circular tablet generally called oval, the tablet in FIG. 9(*b*) shows an elliptical tablet generally called ellipse, the tablet in FIG. 9(*c*) shows a rectangular tablet generally called square, the tablet in FIG. 9(*d*) shows a triangular tablet generally called triangle, the tablet in FIG. 9(*e*) shows a pentangular tablet generally called pentagon, and the tablet in FIG. 9(*f*) shows a hexagonal tablet generally called hexagon.

Figure 10:
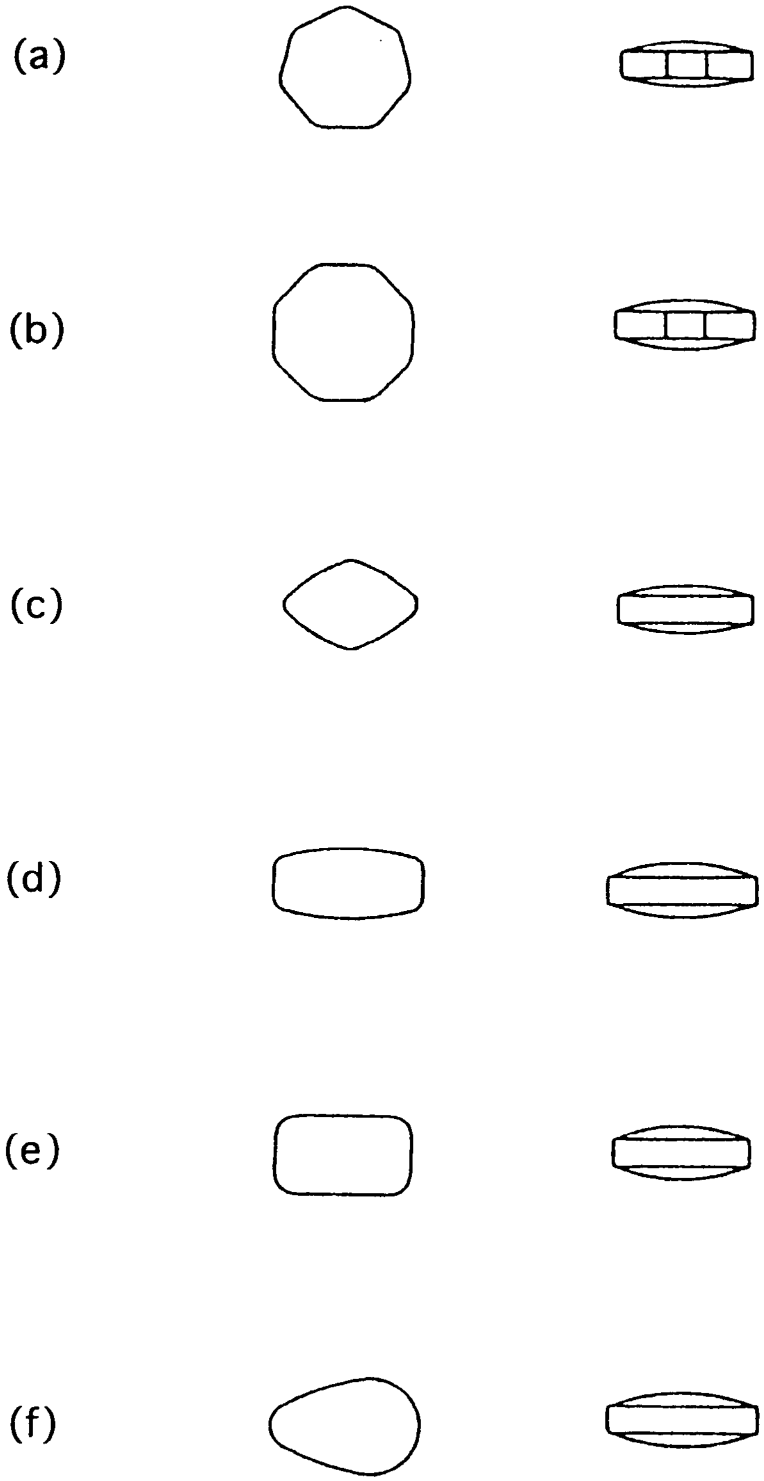
FIG. 10 schematically explains many kinds of tablets produced in experiments. A schematic plane view of each tablet is shown at left and its schematic side view is shown at right.

The tablet in FIG. 10(*a*) shows a heptagonal tablet generally called heptagon, the tablet in FIG. 10(*b*) shows a octagonal tablet generally called octagon, the tablet in FIG. 10(*c*) shows a diamond-shaped tablet generally called diamond, the tablet in FIG. 10(*d*) shows a pillow-shaped tablet generally called pillow or barrel, the tablet in FIG. 10(*e*) shows a rectangular tablet generally called rectangle, and the tablet in FIG. 10*f*) shows an almond-shaped tablet generally called almond.

Figure 11:
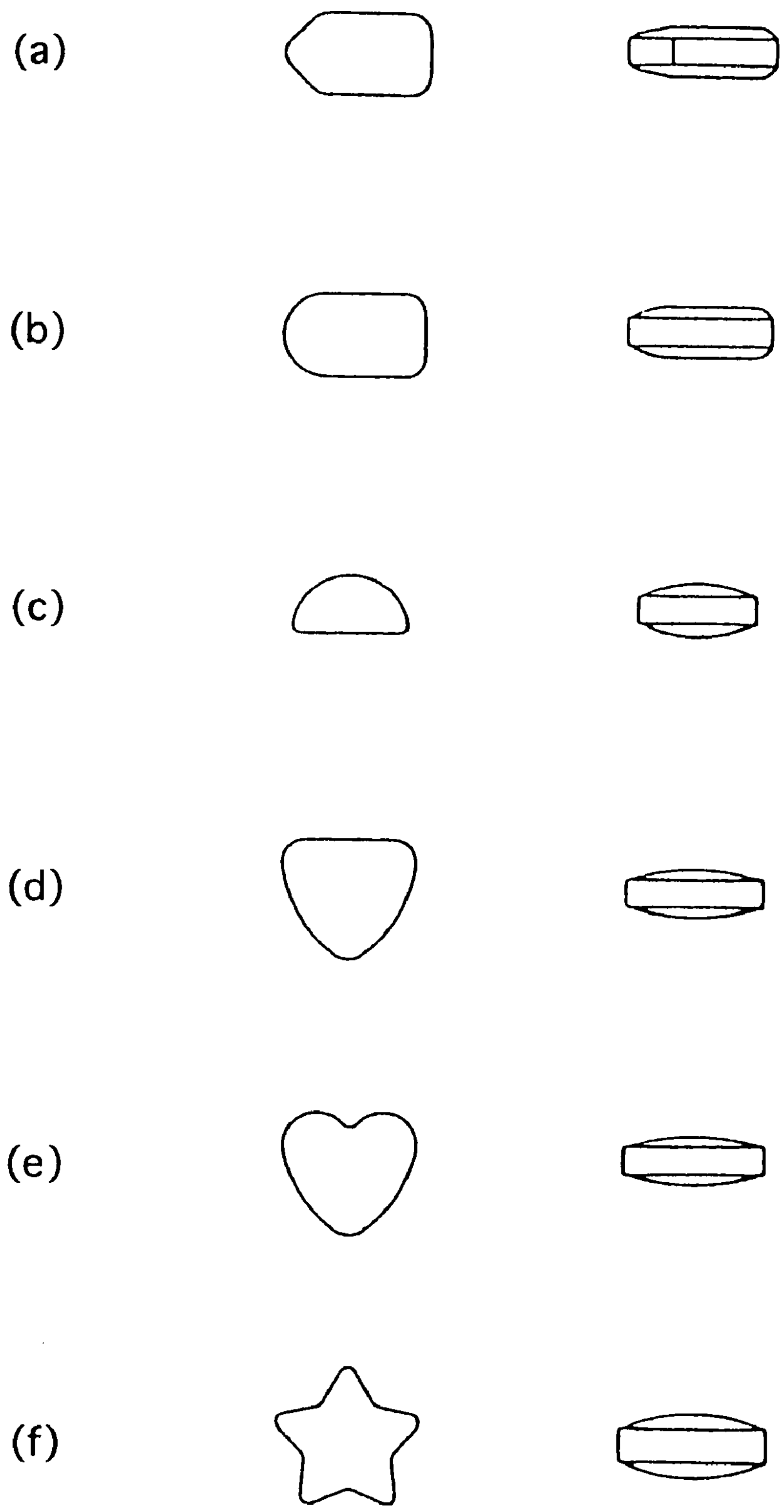
FIG. 11 schematically explains many kinds of tablets produced in experiments. A schematic plane view of each tablet is shown at left and its schematic side view is shown at right.

The tablet in FIG. 11(*a*) shows a sagittal tablet generally called arrowhead, the tablet in FIG. 11(*b*) shows a bullet-shaped tablet generally called bullet, the tablet in FIG. 11(*c*) shows a semilunar tablet generally called half moon, the tablet shown in FIG. 11(*d*) shows a shell-shaped tablet generally called shelled, the tablet in FIG. 11(*e*) shows a heart-shaped tablet generally called heart, and the tablet in FIG. 11(*f*) shows a star-shaped tablet generally called star.

Material was continuously tabletted for 5 hours by means of punches and dies comprising a female mold for the tablets shown in FIG. 7–FIG. 11, obtained tablets were sampled with time, and time for causing sticking was measured by smoothness of the produced tablet's surface. The result was that sticking wasn't happened even after 5 hours.

From the above-mentioned results, it was found that the tablet production method according to the present invention can be preferably used for producing anomalous tablets other than circular tablets.

For tablets using an engraved mark or a dividing line, several dividable tablets were produced like the experiments 1 and 2 except that punches with a projected line for forming a dividing line were used.

Material was continuously tabletted for 5 hours, the produced tablets were sampled with time, and time for happening sticking was measured by smoothness of tablets' surfaces. Sticking wasn't seen even after 5 hours.

Negative pulsating vibration air was used in the above-mentioned experiments. However, pulsating vibration air isn't limited to negative one. When positive pulsating vibration air is used, similar result can be obtained.

In this case, conditions of positive pulsating vibration air aren't specifically limited. The period may be more than or equal to 1 Hz and less than or equal to 10 Hz, its peak may be 10%–15% higher than atmospheric pressure, and its valley may be almost equal to or a litter higher than atmospheric pressure.

In the disclosure of the invention, a system wherein the hopper 15 is connected in midway of the conduit 13 and the compressed air generation means 16 such as a cylinder fully charged with compressed air is connected to the hopper 15 as shown in FIG. 5 is explained. However, the system for discharging lubricant L stored in the hopper 15 to the conduit 13 isn't limited to such a system.

Figure 12:
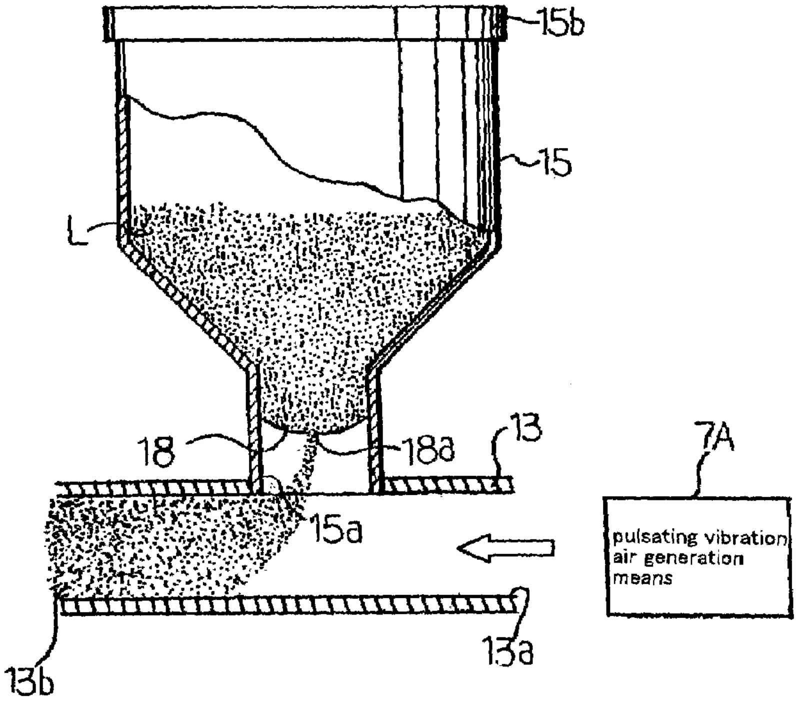
FIG. 12 schematically shows a sectional view of means (metering feeder) for quantitatively supplying molding lubricant contained in a hopper into a conduit.

FIG. 12 explains such a system schematically.

Figure 13:
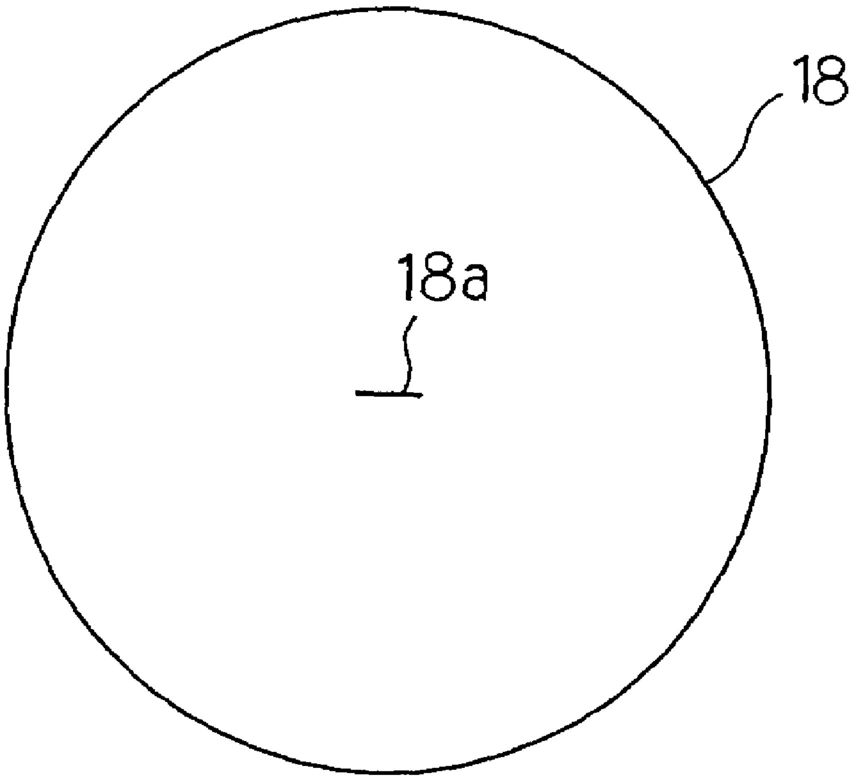
FIG. 13 is a plane view schematically showing one embodiment of an elastic membrane used for the means (metering feeder) in FIG. 12.

According to the system, a pulsating vibration air generation means 7A is connected to one end 13*a* of the conduit, a discharge port 15*a* of the hopper 15 is connected in midway of the conduit 13, and an elastic membrane 18 with an aperture (slit in this example) 18*a* is provided at the discharge port 15*a* so as to be a bottom of the hopper 15 (see FIG. 13).

The elastic membrane 18 is made of rubber such as silicon rubber.

The member shown as 15*b* in the FIG. 12 is a lid and is provided for the hopper 15 removably and airtightly.

Next, operations of the system will be explained.

Figure 14:
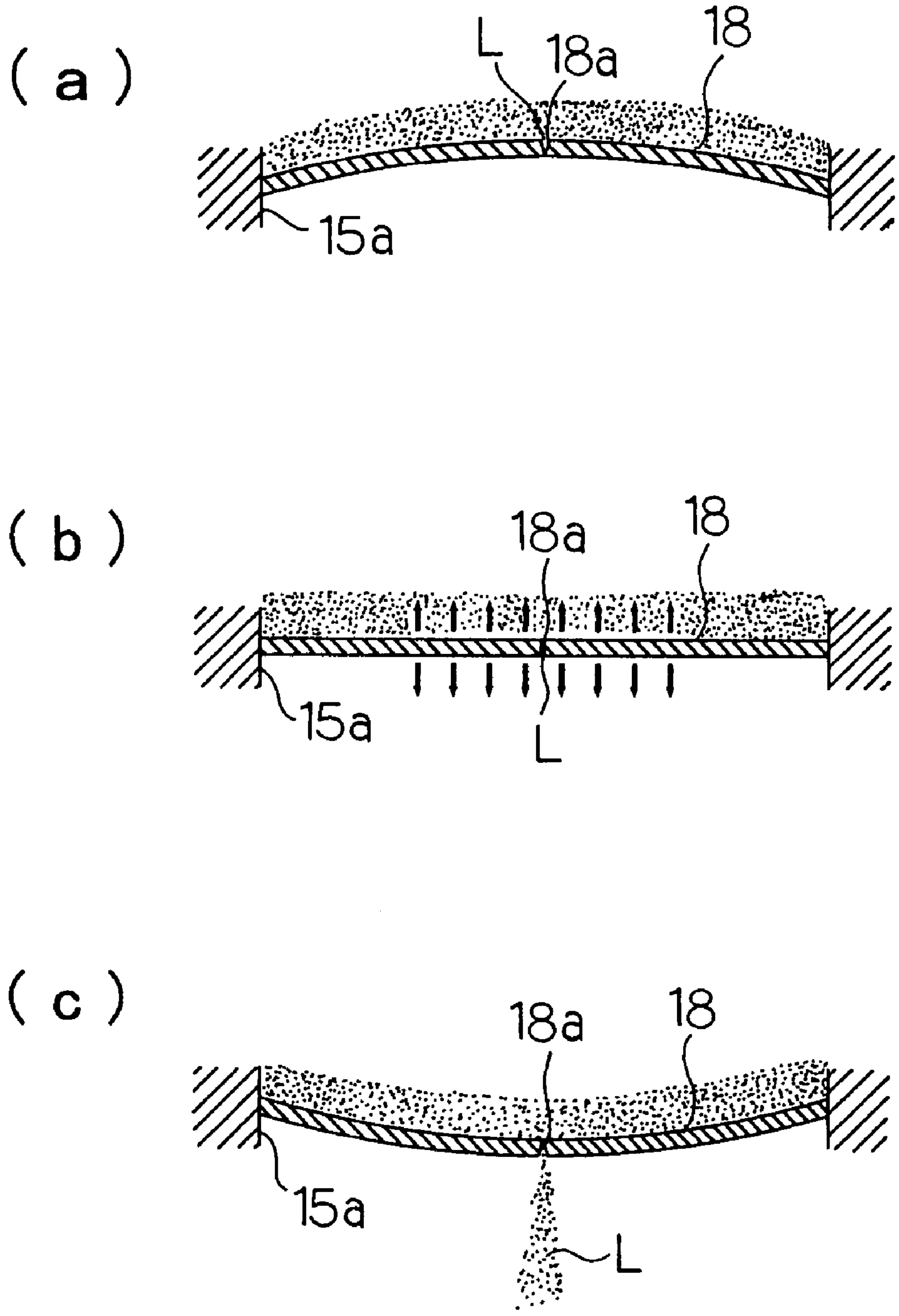
FIG. 14 schematically shows operations of the means (metering feeder) shown in FIG. 12.
Figure 15:
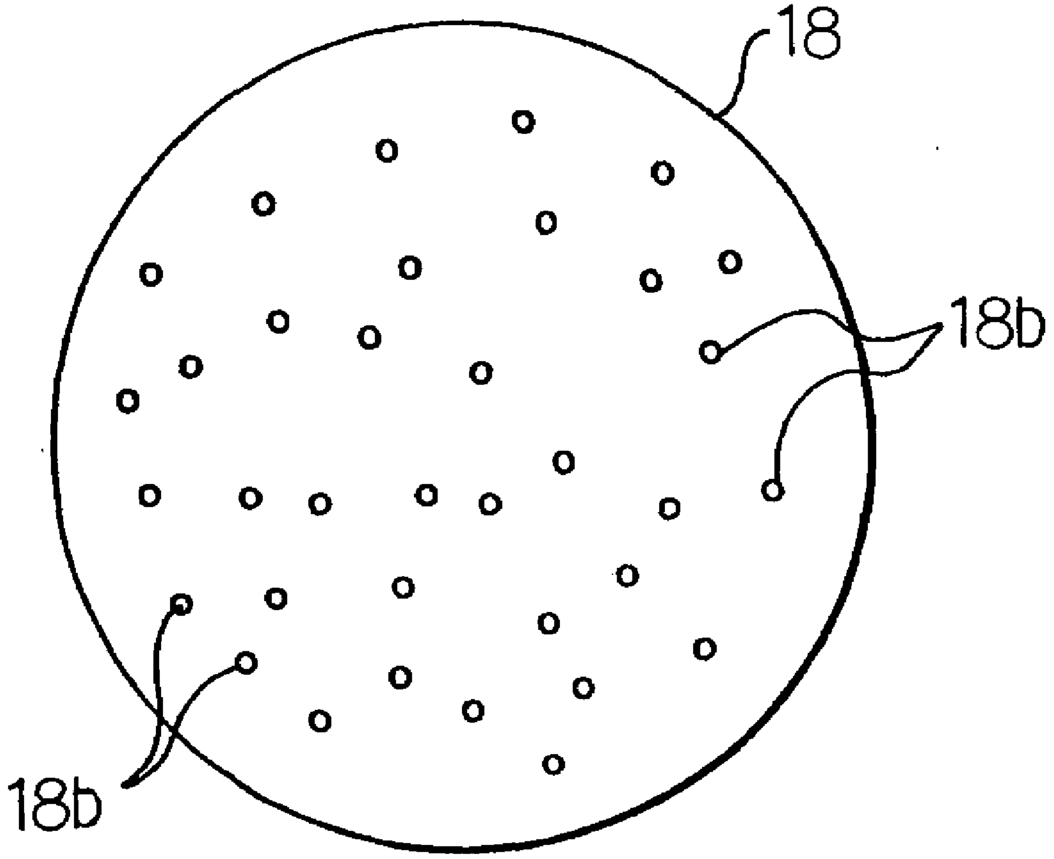
FIG. 15 is a plane view schematically showing another embodiment of an elastic membrane used for the means (metering feeder) in FIG. 12.

FIG. 14 is an explanatory figure schematically showing operation of the system.

For using the system, the lid 15*b* is airtightly attached on the hopper 15 after lubricant L is contained in the hopper 15.

Then, when the pulsating vibration air generation means 7A is driven to supply positive pulsating vibration air to the conduit 13, the air pressure in the conduit 13 becomes higher than that in the hopper 15 while positive pulsating vibration air is at peak side. As shown in FIG. 14(*a*), the elastic membrane 18 is deformed with its center curved upwardly in such a manner that the center becomes an antinode and the circumferential edge becomes a node.

In this case, the section of the aperture (slit in this example) 18*a* becomes V-shaped with is upper end opened. A part of lubricant L stored in the hopper 15 drops in the V-shaped aperture (slit in this example) 18*a*.

As positive pulsating vibration air changes from peak to valley, the air pressure in the conduit 13 is generally lowered so as to be the same as that in the hopper 15. The elastic membrane 18 is going to get back to its original shape because of its resilience as shown in FIG. 14(*b*). The lubricant L dropped in the V-shaped aperture (slit in this example) 18*a* is caught in the aperture 18*a*.

When the positive pulsating vibration air supplied in the conduit 13 is at its valley, the air pressure in the conduit 13 becomes lower than that in the hopper 15 and the elastic membrane 18 is deformed with its center curved downwardly in such a manner that the center is antinode and the circumferential edge is node.

In this case, the section of the aperture (slit in this example) 18*a* becomes reverse V-shaped with its lower end opened. The lubricant L caught in the aperture 18*a* is discharged to the conduit 13.

Then the lubricant L discharged in the conduit 13 is immediately mixed with positive pulsating vibration air supplied in the conduit 13 to be dispersed in the conduit 13 and is pneumatically transported to a spraying chamber (refer to the spraying chamber 8 in FIG. 5).

The elastic membrane 18 repeats up and down vibration as shown in FIG. 14(*a*)–FIG. 14(*c*) according to vibration amplitude, wave length, wave shape, and vibration frequency of positive pulsating vibration air.

Therefore, as long as vibration amplitude, wave length, wave shape, and vibration frequency of positive pulsating vibration air supplied in the conduit 13 are fixed, the elastic membrane 18 vibrates up and down at a fixed vibration amplitude and frequency. Accordingly the amount of lubricant L discharged in the conduit 13 via the aperture (slit in this sample) 18*a* is constant.

Further according to this system, because positive pulsating vibration air is supplied in the conduit 13, there are no phenomenon such as adhesion of powdered material on the inner wall of the conduit 13 and blowing-out of powdered material in the conduit 13 which have been seen in the case that steady air pressure is used for pneumatically transporting powdered material.

Therefore, according to this system, lubricant L is discharged from the other end 13*b* of the conduit 13 at the same density as the lubricant L discharged in the conduit 13.

In other words this system can be functioned as a metering feeder.

Therefore, when the other end 13*b* of the conduit 13 is connected to the spraying chamber (refer to spraying chamber 8 in FIG. 5), as long as the size of the aperture (slit in this example) 18*a* is fixed, and vibration amplitude, wave length, wave shape, and vibration frequency of positive pulsating vibration air supplied in the conduit 13 are fixed, lubricant L with constant density can be always supplied in the spraying chamber (refer to spraying chamber 8 in FIG. 5).

Further, a media for pneumatically transporting lubricant L is air even if it is a positive pulsating vibration air so that the amount of lubricant L mixed with positive pulsating vibration air can be extremely minimized.

Accordingly, because a minute amount of lubricant L can be always sprayed in stable condition in the spraying chamber (refer to spraying chamber 8 in FIG. 5), minute amount of lubricant L can be applied on the surfaces of the punches (the surface (lower surface) 3*s* of the upper punch and the surface (upper surface) 4*s* of the lower punch 4 as shown in FIG. 2) and the surface (inner wall) is of the die 1.

In FIG. 12, the elastic membrane has a slit 18*a*, however, this is only a preferable example. The aperture provided for the elastic membrane isn't limited to the slit 18*a* and the aperture may be small ones or the number isn't limited to one.

When the size and the number of the aperture or conditions (vibration amplitude, wave length, wave shape, and vibration frequency) of positive pulsating vibration air supplied in the conduit 13 are varied, the density of lubricant L supplied in the spraying chamber (refer to the spraying chamber 8 in FIG. 5) can be changed diversely.

In this embodiment, a rotary type pulsating vibration air generation means 7A shown in FIG. 3(*b*) and FIG. 5(*b*) wherein a valve element 73 is provided rotatably around a rotary axis 74 so as to divide inside of the tube 72 into two parts is explained as a pulsating vibration air generation means. However, it isn't limited to such means 7A.

Figure 16:
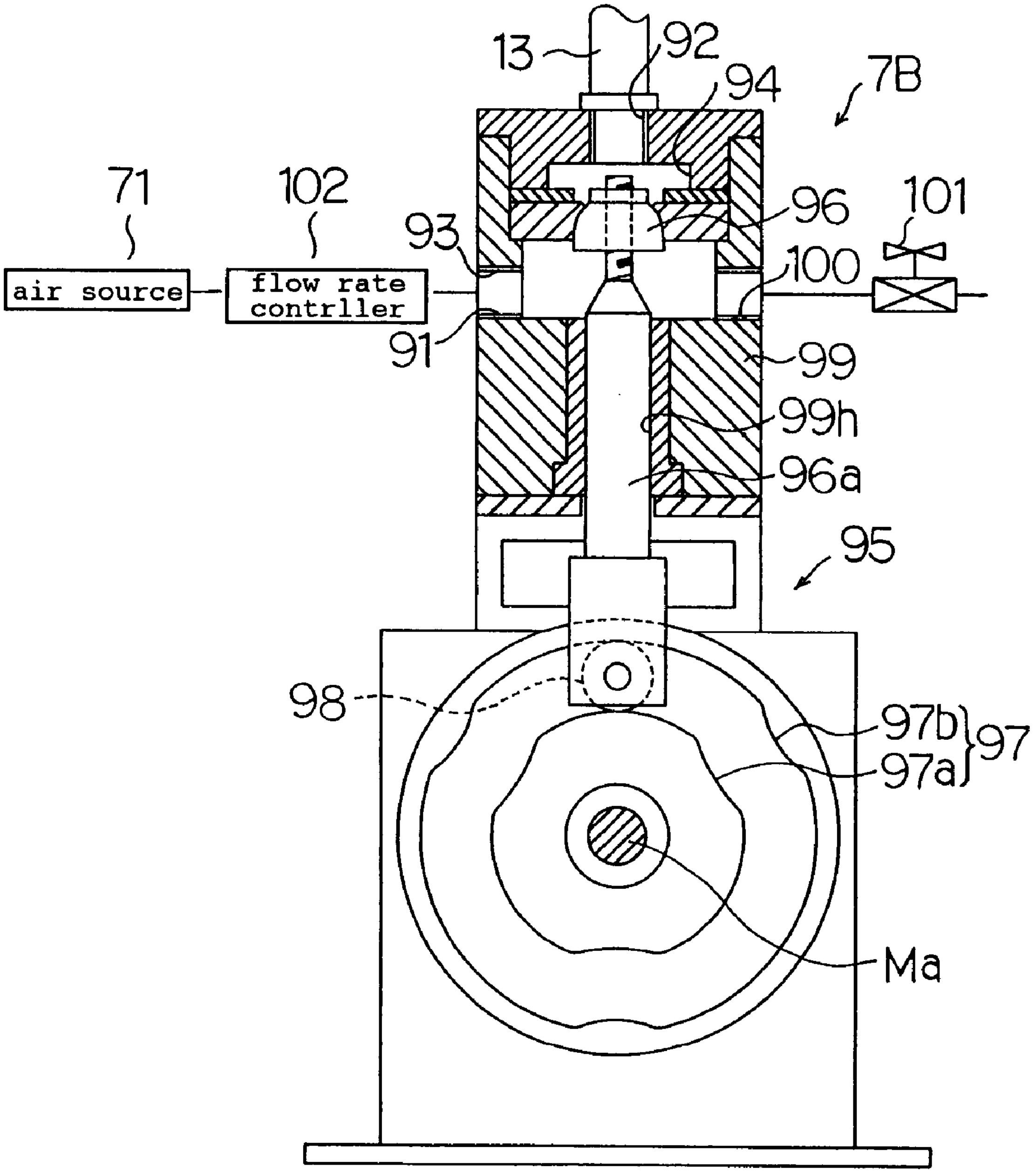
FIG. 16 is a sectional view schematically showing another embodiment of pulsating vibration air generation means.
Figure 17:
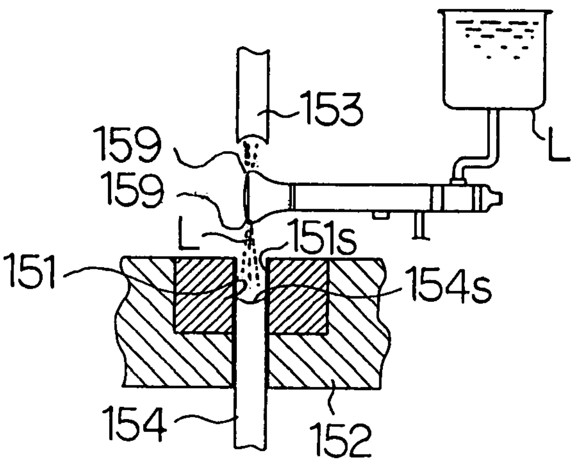
FIG. 17 schematically shows procedures of the prior tablet production method disclosed in JP-B-41-11273.
Figure 17:
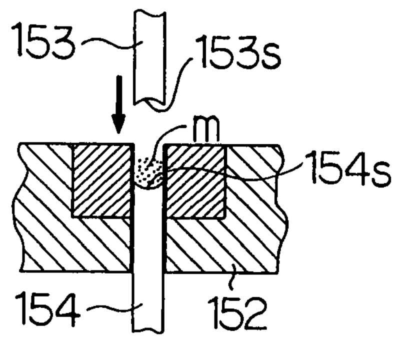
Figure 17:
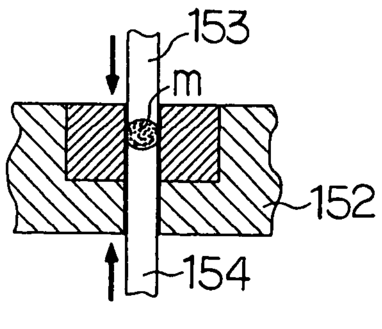
Figure 18:
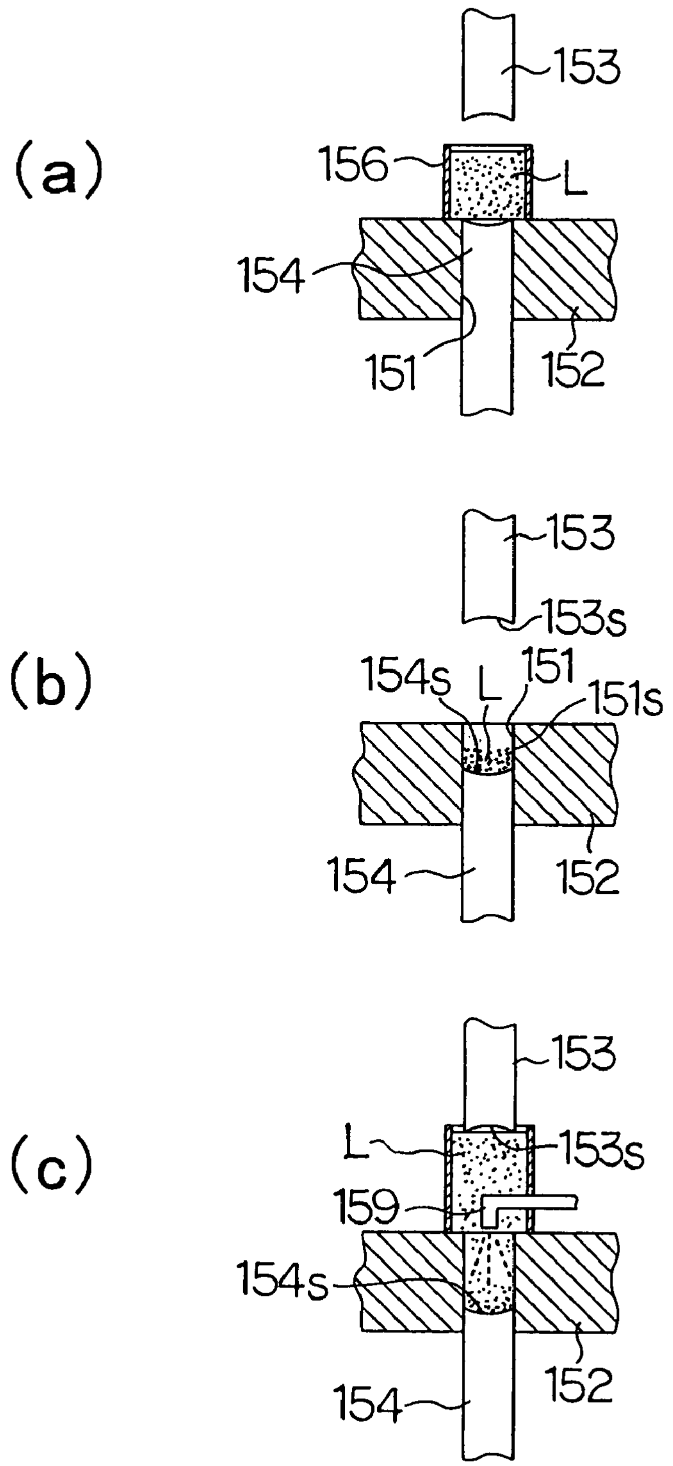
FIG. 18 schematically shows procedure of the prior tablet production method disclosed in JP-A-56-14098.

FIG. 16 shows a section of other embodiment of pulsating vibration air generation means.

The high pressure pulsating vibration air generation means 7B is provided with a valve chamber 94 having a valve seat 94 between an input port 91 and an output port 92 and a valve plug 96 which opens and closes by a cam mechanism 95.

The cam mechanism 95 is provided with a rotary cam 97 rotatable by a driving means such as a motor (not shown) and a roller 98 attached at the lower end of the valve plug 96.

The valve seat 93 is formed with a hole narrowing into the output port 92 and the valve plug 96 is formed like a reverse mortar so as to conform to the shape of the valve seat 93 and designed to airtightly close the valve seat 93.

Further in this embodiment, an axis 96*a* of the valve plug 96 is provided in an axis hole 99*h* of a case 99 so as not to leak air and so as to be movably up and down.

The roller 98 is rotatably pinched by the rotary cam 97 and moves up and down according to a concavo-convex pattern on the rotary cam 97 while rotating.

More detailed, the rotary cam 97 is provided with an inner rotary cam 97*a* and an outside rotary cam 97*b*.

Concavo-convex pattern is provided for the inner rotary cam 97*a* and the outside rotary cam 97*b* respectively so as to keep distance of the roller 98 and to keep in line each other.

The roller 98 is pinched between the inner rotary cam 97*a* and the outside rotary cam 97*b* and is moved up and down while rotating according to the concavo-convex pattern provided for the inner rotary cam 97*a* and the outside rotary cam 97*b* by rotating the rotary cam 97 without causing jumping of the valve plug 96.

The convavo-convex pattern provided for the rotary cam 97 is selected according to physical property of lubricant L stored in the hopper 15.

In this embodiment, a flow rate control means 102 is provided for the input port 91 and compressed air which is generated by an air source 71 and of which flow rate is adjusted properly by the flow rate control means 102 is supplied in the input port 91.

Further, one end of a conduit (the conduit 13 shown in FIG. 3 or FIG. 5) is connected to the output port 92.

The numeral 100 in FIG. 5 shows a flow rate control port provided if required. An output control valve 101 for adjusting pressure of pulsating vibration air generated from the output port 92 is provided so as to be adjustable at a desired condition from full communication to atmospheric air and shut down from atmospheric air.

Next, operational procedure for generating positive pulsating vibration air having a desired period, vibration amplitude, and wave shape by means of the high pressure pulsating vibration air generation means 7B will be explained.

The rotary cam 97 which is easy to mix lubricant L with air according to physical property of lubricant L stored in the hopper 15 is attached to a rotary axis Ma of a driving means (not shown) of the high pressure pulsating vibration air generation means 7B.

Then the air source 71 is driven and a fixed amount of compressed air is supplied to the input port 92 by adjusting the flow rate control means 102.

Further, the rotary cam 97 is rotated at a fixed rotational velocity by actuating the driving means (not shown).

The pressure of pulsating vibration air discharged from the output port 92 is adjusted by adjusting the output control valve 101, if required.

When the rotary cam 97 is rotated at a fixed rotational velocity, the valve plug 96 moves up and down according to the concavo-convex pattern of the rotary cam 97. Therefore, when the valve seat 93 is controlled at full closed, half opened, or full opened according to the concavo-convex pattern of the rotary cam 97, pulsating vibration air with a desired wave shape can be outputted from the output port 92.

According to the high pressure pulsating vibration air generation means 7B, rotational velocity of the rotary cam 97 may be changed by controlling the driving means (not shown) in order to obtain a desired period of pulsating vibration air discharged from the output port 92. Further, the air source 71, the flow rate control means 102, and/or the output control valve 101 may be appropriately controlled in order to obtain a desired vibration amplitude of pulsating vibration air discharged from the output port 92.

INDUSTRIAL APPLICABILITY

As mentioned above, according to the tablet production method as set forth in claim 1, as lubricant is sprayed in a spraying chamber generating pulsating vibration air and lubricant mixed with pulsating vibration air is applied on the surfaces of punches and dies, lubricant can be uniformly applied on the surfaces of punches and dies comparing with the prior external lubricant spraying method.

As a result, in a process of tabletting compound powdered or granulated which is denaturalized or inactivated when tabletted at high pressure, compound powdered or granulated which is denaturalized or inactivated when tabletted at high pressure is hard to be attached on the surfaces of punches and dies and also sticking, capping, laminating, and so on are hardly happened for the produced tablets of biological pharmaceuticals.

Further, lubricant is only attached on the surfaces of tablets and isn't included inside therein. So, comparing with the tablet including lubricant therein, when compound powdered or granulated which is denaturalized or inactivated when tabletted at high pressure is tabletted at a low tabletting pressure (concretely at tabletting pressure less than 1 ton/$cm^2$), the produced tablet has practical hardness.

According to the tablet production method as set forth in claim 2, as lubricant is sprayed in a spraying chamber generating pulsating vibration air and lubricant mixed with pulsating vibration air is applied on the surfaces of punches and dies, lubricant can be uniformly applied on the surfaces of punches and dies comparing with the prior external lubricant spraying method.

As a result, in a process of tabletting solid dispersion powdered or granulated, molding material is hard to be adhered on the surfaces of punches and dies and also sticking, capping, laminating, and so on are hardly happened for the produced tablets of solid dispersion.

Further, lubricant is only attached on the surfaces of produced tablets of solid dispersion and isn't included inside therein. So, comparing with the tablet of solid dispersion including lubricant therein, when solid dispersion powdered or granulated is tabletted at a low tabletting pressure, the produced tablet of solid dispersion has practical hardness.

Therefore, according to this tablet production method, a tablet of solid dispersion can be produced at low tabletting pressure so that physical property of solid dispersion doesn't change.

According to the tablet production method as set forth in claim 3, as lubricant mixed with positive pulsating vibration air is sprayed in a spraying chamber to be applied on the surfaces of the punches and dies, lubricant can be uniformly applied thereon comparing with the prior external lubricant spraying method.

As a result, in a process of tabletting compound powdered or granulated which is denaturalized or inactivated when tabletted at high pressure, compound powdered or granulated which is denaturalized or inactivated when tabletted at high pressure is hard to be attached on the surfaces of punches and dies and also sticking, capping, laminating, and soon are hardly caused for the produced tablets of biological pharmaceuticals.

Further, lubricant is only attached on the surfaces of tablets and isn't included inside therein. So, comparing with the tablet including lubricant therein, when compound powdered or granulated which is denaturalized or inactivated when tabletted at high pressure is tabletted at a low tabletting pressure (concretely at tabletting pressure less than 1 ton/$cm^2$), the produced tablet has practical hardness.

According to the tablet production method as set forth in claim 4, as lubricant mixed with positive pulsating vibration air is sprayed in a spraying chamber to be applied on the surfaces of punches and dies, lubricant can be uniformly applied thereon comparing with the prior external lubricant spraying method.

As a result, in a process of tabletting solid dispersion powdered or granulated, molding material is hard to be adhered on the surfaces of punches and dies and also sticking, capping, laminating, and so on are hardly caused for the produced tablets of solid dispersion.

Further, lubricant is only attached on the surfaces of produced tablets of solid dispersion and isn't included inside therein. So, comparing with the tablet of solid dispersion including lubricant therein, when solid dispersion powdered or granulated is tabletted at a low tabletting pressure, the produced tablet of solid dispersion has practical hardness.

Therefore, according to this tablet production method, tablet of solid dispersion can be produced at low tabletting pressure so that physical property of solid dispersion doesn't change.

According to the tablet production method as set forth in claim 5, the spraying amount of lubricant per tablet is greater than or equal to 0.0001 weight percent and less than or equal to 0.2 weight percent. Therefore, disintegrating time of tablet doesn't extend or its hardness isn't deteriorated.

According to the tablet production method as set forth in claim 6, as the punches are provided with a projected line for forming a dividing line of a tablet, a dividable tablet including compound powdered or granulated which is denaturalized or inactivated when tabletted at high pressure and a dividable tablet including solid dispersion powdered or granulated of which functions aren't damaged can be easily produced.

According to the tablet production method as set forth in claim 7, as material is continuously tabletted at tabletting procedure by utilizing that sticking and so on aren't happened, a tablet including powdered or granular compound which is denaturalized or inactivated when tabletted at high pressure can be produced at industrial production base.

According to the tablet production method as set forth in claim 8, as material is continuously tabletted at tabletting procedure by utilizing that sticking and so on aren't happened, tablet including solid dispersing powdered or granular material can be produced at industrial production base.

According to the tablet production method in claim 9, as the tabletting pressure for molding material is low, even if granule included in a tablet is powdered or granular material including compound which is denaturalized or inactivated when tabletted at high pressure, tablet can be produced without denaturalizing or deactivating the compound.

Further, if granule included in a tablet is solid dispersion powdered or granulated, a tablet can be produced without destroying functions of solid dispersion powdered or granulated.

According to the tablet in claim 10, as lubricant is attached only on the surface of the tablet, disintegrating time of the tablet caused by water repellency of lubricant doesn't delay.

Further, as this tablet doesn't include lubricant therein, it is tabletted at low tabletting pressure. Therefore, compound powdered or granulated which is denaturalized or inactivated when tabletted at high pressure isn't denaturalized or inactivated.

According to the tablet described in claim 11, as lubricant is only attached on the surface of the tablet, delay of disintegrating time of the tablet caused by water repellency of lubricant isn't happened.

Further, as this tablet doesn't include lubricant therein, it is tabletted at low tabletting pressure. Therefore, functions of solid dispersion powdered or granulated isn't damaged.

According to the tablet described in claim 12, only a minute amount of lubricant is attached on the surface of the tablet, disintegrating time of the tablet caused by water repellency of lubricant doesn't delay.

Therefore, if such a tablet (uncoated tablet) is used as an uncoated tablet, it becomes a rapidly soluble tablet. It is suitable as a tablet which is desired to be disintegrated immediately at an objective place. If a film which is dissolved at an objective place is coated on the surface of the tablet, the tablet can be rapidly dissolved at the objective place when the film is melted. Therefore, such a tablet can be used as a tablet which is desired to be dissolved at an objective place.

According to the tablet as set forth in claim 13, as the shape of the tablet is anomalous, drugs (active agent) included in tablets can be easily distinguished from the shape. As a result, medication error is hardly caused for these tablets.

According to the tablet as set forth in claim 14, as a dividing line is provided for the surface of the tablet, dividable tablet which can be dissolved at an objective place can be supplied in the market.

What is claimed is:

1. A method for producing compressed tablets, comprising:

selecting powdered or granular material comprising an active compound which is denaturalized or inactivated when compressed at a pressure greater than or equal to 1 ton/$cm^2$, providing a spraying chamber housing a punch and a die, generating pulsating vibration air, spraying, within a spraying chamber, a lubricant admixed with said pulsating vibration air to apply the lubricant on surfaces of said punch and die, mixing said powdered or granular material with a diluting agent to make a molding material, said molding material not containing said lubricant, and compressing said molding material using said lubricated punch and said lubricated die surfaces at a pressure less than 1 $ton/cm^2$ to produce compressed tablets, wherein sprayed lubricant is incorporated in said tablets at an amount not less than 0.0001 weight percent and not greater than 0.2 weight percent.

2. A method for producing compressed tablets, comprising:

selecting powdered or granular material containing a dispersed active agent, said active agent being a low molecule compound of which elution is delayed when compressed at a pressure greater than or equal to 1 $ton/cm^2$ or a high molecule compound which is decomposed or denaturalized when compressed at a pressure greater than or equal to 1 $ton/cm^2$, providing a spraying chamber housing a punch and a die, generating pulsating vibration air, spraying, within said spraying chamber, a lubricant admixed said pulsating vibration air to apply the lubricant on surfaces of said punch and die, mixing said powdered or granular material with said diluting agent to make a molding material, said molding material not containing said lubricant, and compressing said molding material using said lubricated punch and die surfaces at a pressure less than 1 $ton/cm^2$ to produce compressed tablets, wherein the sprayed lubricant is incorporated in said tablets at an amount not less than 0.0001 weight percent and not greater than 0.2 weight percent.

3. A method for producing compressed tablets, comprising:

selecting powdered or granular material comprising an active compound which is denaturalized or inactivated when compressed at a pressure greater than or equal to 1 $ton/cm^2$, providing a spraying chamber housing a punch and a die, applying lubricant on surfaces of said punch and die by spraying, within said spraying chamber, an admixture of the lubricant and positive pulsating vibration air, mixing said powdered or granular material with a diluting agent to make a molding material, said molding material not containing said lubricant, and compressing said molding material using said lubricated punch and said lubricated die surfaces at a pressure less than 1 $ton/cm^2$ to produce compressed tablets, wherein the sprayed lubricant is incorporated in said tablets at an amount not less than 0.0001 weight percent and not greater than 0.2 weight percent.

4. A method for producing compressed tablets, comprising:

selecting powdered or granular material containing a dispersed active agent, said active agent being a low molecule compound of which elution is delayed when compressed at a pressure greater than or equal to 1 $ton/cm^2$ or a high molecule compound which is decomposed or denaturalized when compressed at a pressure greater than or equal to 1 $ton/cm^2$, providing a spraying chamber housing a punch and a die, applying the lubricant on surfaces of said punch and die by spraying, within said spraying chamber, an admixture of the lubricant and positive pulsating vibration air, mixing said powdered or granular material with a diluting agent to make a molding material, said molding material not containing said lubricant, and compressing said molding material using said lubricated punch and said lubricated die surfaces at a pressure less than 1 $ton/cm^2$ to produce compressed tablets, wherein the sprayed lubricant is incorporated in said tablets at an amount not less than 0.0001 weight percent and not greater than 0.2 weight percent.

5. The method according to any one of claims 1–4, wherein said lubricant is stearate acid metal salt.

6. The method according to any one of claims 1–4, wherein said lubricated surface of said punch is provided with a projecting line that forms a dividing line on said tablets.

7. The method according to any of claims 1–4 wherein said pulsating vibration air is generated, said lubricant is admixed with said pulsating vibration air, and said mixture of lubricant and pulsating vibration air is sprayed into said spraying chamber simultaneously.

8. The method according to any one of claims 1–4, wherein said diluting agent is a saccharide.

9. A tablet comprising:

powdered or granular material including an active compound which is denaturalized or inactivated when compressed at a pressure greater than or equal to 1 $ton/cm^2$, a diluting agent, and a lubricant, said tablet having been compressed at a pressure less than 1 $ton/cm^2$ and containing a tabletting lubricant only on a surface thereof and not within said tablet, said tabletting lubricant being contained in an amount not less than 0.0001 weight percent and not greater than 0.2 weight percent, and wherein the active compound in said tablet has higher activity than active compound in a tablet of same materials compressed at same pressure but which contains said lubricant within the tablet.

10. A tablet comprising:

(i) powdered or granular material containing a dispersed active agent, said active agent being a low molecule compound of which elution is delayed when compressed at a pressure greater than or equal to 1 $ton/cm^2$ or a high molecule compound which is decomposed or denaturalized when compressed at a pressure greater than or equal to 1 $ton/cm^2$, (ii) a diluting agent, and (iii) a lubricant, said tablet having been compressed at a pressure less than 1 $ton/cm^2$ and containing a tabletting lubricant only on a surface thereof and not within said tablet, said tabletting lubricant being contained in an amount not less than 0.0001 weight percent and not greater than 0.2 weight percent, and wherein the active compound in said tablet has higher activity than active compound in a tablet of the same materials compressed at same pressure but which contains said lubricant within the tablet.

11. The tablet as set forth in claim 9 or 10, wherein the tablet has a dividing line on a surface thereof.

12. The method according to any of claims 1–4, wherein said tablets have a hardness of at least 7 kgf.

13. The tablet according to either of claim 9 or 10, which have a hardness of at least 7 kgf.

14. The tablet according to either of claim 9 or 10, wherein said tabletting lubricant is stearate acid metal salt.

* * * * *

CERTIFICATE OF CORRECTION

PATENT NO. : 6,964,779 B1
DATED : November 15, 2005
INVENTOR(S) : Eiji Hayakawa et al.

It is certified that error appears in the above-identified patent and that said Letters Patent is hereby corrected as shown below:

Column 3,
Line 15, "in activated" should read -- inactivated --.

Column 4,
Line 28, "lubricant" should read -- lubricants --.

Column 5,
Line 25, "metylcellulose" should read -- methylcellulose --.

Column 7,
Line 43, "Therefore" should read -- Therefore, --;
Line 45, "deteriorated." should read -- deteriorate. --;
Line 47, "of" should be deleted;
Lines 51 and 53, "including" should read -- includes --; and
Line 57, "executed;" should read -- executed: --.

Column 8,
Line 5, "executed;" should read -- executed: --; and
Line 44, "isn't happened." should read -- does not happen. --.

Column 15,
Line 34, "wasn't" should read -- had not --; and
Lines 35 and 36, "was" should read -- had --.

Column 17,
Line 62, "were" should read -- had --.

Column 18,
Line 2, "hours." should read -- hour --;
Line 18, "were" should read -- had --; and
Line 39, "a" (second occurrence) should be deleted.

Column 19,
Line 6, "wasn't" should read -- had not --; and
Line 62, "is" should read -- its --.

Column 20,
Line 28, "Accordingly" should read -- Accordingly, --.

UNITED STATES PATENT AND TRADEMARK OFFICE

CERTIFICATE OF CORRECTION

PATENT NO. : 6,964,779 B1 
DATED : November 15, 2005
INVENTOR(S) : Eiji Hayakawa et al.

It is certified that error appears in the above-identified patent and that said Letters Patent is hereby corrected as shown below:

Column 22,
Line 15, "controlled at full closed" should read -- is fully closed --;
Line 16, "full opened" should read -- fully opened, --; and
Lines 44 and 63, "are hardly happened" should read -- hardly happen --.

Column 23,
Line 66, "aren't" should read -- have not --.

Column 24,
Line 30, "isn't" should read -- has not --; and
Line 50, "for" should read -- by --.

Column 25,
Line 22, "admixed" should read -- admixed with --.

Column 26,
Line 14, "claims 1-4" should read -- claims 1-4, --; and
Line 62, "have" should read -- has --.

Signed and Sealed this

Ninth Day of May, 2006

JON W. DUDAS
*Director of the United States Patent and Trademark Office*